United States Patent
Pokkuluri et al.

(10) Patent No.: US 10,487,368 B2
(45) Date of Patent: Nov. 26, 2019

(54) STABILIZATION OF RUBISCO ACTIVASE FOR ENHANCED PHOTOSYNTHESIS AND CROP YIELDS

(71) Applicant: UCHICAGO ARGONNE, LLC, Chicago, IL (US)

(72) Inventors: Phani R. Pokkuluri, Westmont, IL (US); Marianne Schiffer, Downers Grove, IL (US); Andrej Joachimiak, Bolingbrook, IL (US); Rosemarie Wilton, Elmhurst, IL (US)

(73) Assignee: UChicago Argonne, LLC, Chicago, IL (US)

( * ) Notice: Subject to any disclaimer, the term of this patent is extended or adjusted under 35 U.S.C. 154(b) by 77 days.

(21) Appl. No.: 15/690,247

(22) Filed: Aug. 29, 2017

(65) Prior Publication Data
US 2018/0094328 A1   Apr. 5, 2018

Related U.S. Application Data

(60) Provisional application No. 62/402,227, filed on Sep. 30, 2016.

(51) Int. Cl.
*C12N 15/82* (2006.01)
*C12N 9/88* (2006.01)

(52) U.S. Cl.
CPC ........ *C12Y 401/01039* (2013.01); *C12N 9/88* (2013.01)

(58) Field of Classification Search
CPC .............................. C12Y 401/01039
See application file for complete search history.

(56) References Cited

U.S. PATENT DOCUMENTS

| | | |
|---|---|---|
| 7,098,393 B2 | 8/2006 | Fleurial et al. |
| 7,314,975 B2 | 1/2008 | Kurek et al. |
| 7,557,267 B2 | 7/2009 | Kurek et al. |
| 7,723,573 B2 | 5/2010 | Kurek et al. |
| 9,177,764 B1 | 11/2015 | Baney |
| 2010/0077502 A1 | 3/2010 | Broekaert et al. |

OTHER PUBLICATIONS

Scafaro, A. et al., New Phytologist; 2016, vol. 211, pp. 899-911.*
Kurek, I., et al., The Plant Cell Oct. 2007; vol. 19, pp. 3230-3241. (Year: 2007).*
Duanmu, Q., et al., "Effects of Ion Barrier Film on Image Noise in Generation III Image Tube," International Conference on Optoelectronics and Microelectronics, Aug. 23-25, 2012, pp. 549-552.
Jiang, D., et al., "Electron transmittance characteristics of MCP ion barrier film," Proceedings of SPIE, vol. 5633, Advanced Materials and Devices for Sensing and Imaging II, Jan. 20, 2005, pp. 443-446.
Zhang, N., et al., "The Research on Preparation Process Optimization of Ion Barrier Film on the Input Side of MCP," Key Engineering Materials, vol. 552, May 27, 2013, pp. 186-192.
Barta, et al., "Rubisco Activase Activity Assays," Methods in Molecular Biology: Photosynthesis Research Protocols, pp. 375-382 (2010).
Kumar, et al., "*Arabidopsis thaliana* expressing a thermostable chimeric Rubisco activase exhibits enhanced growth and higher rates of photosynthesis at moderately high temperatures," Photosynthesis Research 100(3), pp. 143-153 (2009).
Kurek, et al., "Enhanced Thermostability of *Arabidopsis rubisco* Activase Improves Photosynthesis and Growth Rates under Moderate Heat Stress," The Plant Cell 19, pp. 3230-3241 (2007).
Li, et al., "Identification of critical argmme residues in the functioning of Rubisco activase," Archives of Biochemistry and Biophysics 450(2), pp. 176-182 (2006).
Lobell, et al., "Climate trends and global crop production since 1980," Science 333(6042), pp. 616-620 (2011).
Pokkuluri, et al., "Increasing protein stability by polar surface residues: domain-wide consequences of interactions within a loop," Biophysical Journal 82(1), pp. 391-398 (2002).
Portis, "Rubisco activase—Rubisco's catalytic chaperone," Photosynthesis Research 75(1), pp. 11-27 (2003).
Scales, et al., "A non-radioactive method for measuring Rubisco activase activity in the presence of variable ATP: ADP ratios, including modifications for measuring the activity and activation state of Rubisco," Photosynthesis Research 119(3), pp. 355-365 (2014).

* cited by examiner

*Primary Examiner* — Russell Kallis
(74) *Attorney, Agent, or Firm* — Foley & Lardner LLP

(57) ABSTRACT

A modified rubisco activase, wherein the modified rubisco activase has a melting temperature greater than that of wild type rubisco activase. Further aspects of the disclosure relate to an isolated polynucleotide encoding a modified rubisco activase and a recombinant expression system comprising the isolated polynucleotide. Still further aspects of the disclosure relate to a plant cell transfected with the recombinant expression system. Certain aspects of the disclosure relate to a genetically modified plant expressing the isolated polynucleotide encoding a modified rubisco activase.

24 Claims, 8 Drawing Sheets
Specification includes a Sequence Listing.

FIGURE 1

```
CLUSTAL multiple sequence alignment by Kalign (2.0)

tobacco          --AEQIDVDPKKQTDSDRWKGLVQDFSDDQQDITRGKGMVDSLFQAPTGTGTHHAVLQSY
Athaliana        ------AVKEDKQTDGDRWRGLAYDTSDDQQDITRGKGMVDSVFQAPMGTGTHHAVLSSY
Soyshort         AVEEKKEIEETQQTDKDRWKGLAYDISDDQQDITRGKGLVDSLFQAPQDAGTHYAVMSSY
Soylong          --AAEKEIDEKQQTDKDRWKGLAYDVSDDQQDITRGKGLVDSLFQAPQDTGTHYAIMSSY
Miscanth_short   ---AAKEVDETKETDGDRWKGLAFDISDDQQDITRGKGMIDSLFQAPMGDGTHVAVLSSY
Miscanth_long    AMAVNKEVDETKQTEQDRWRGLAYDTSDDQQDITRGKGRVDPLFQAPMGDGTHVAVLSSY
                               ↓ AAA+ domain start
tobacco          EYVSQGLRQYNLDNKLDGFYIAPAFMDKLVVHITKNFLKLPNIKVPLILGIWGGKGQGKS
Athaliana        EYVSQGLRQYNLDNMMDGFYIAPAFMDKLVVHITKNFLTLPNIKVPLILGIWGGKGQGKS
Soyshort         EYLSTGLRQY-LDNKMDGFYIAPAFMDKLVVHISKNFMTLPNIKVPLILGIWGGKGQGKS
Soylong          EYLSTGLKQYNLDNNMDGFYIAPAFMDKLVVHISKNFMTLPNIKVPLILGIWGGKGQGKS
Miscanth_short   DYISQGQKTYSMDNTMDGFYIARGFMDKLVVHLSKNFMKLPNIKVPLILGIWGGKGQGKS
Miscanth_long    DYISQGLRQYSFDNTMDGYYIAPAFMDKLVVHIAKNFMTLPNIKVPLILGIWGGKGQGKS tobacco          FQCELVFRKMGINPIMMSAGELESGNAGEPAKLIRQRYREAAEIIRKGNMCCLFINDLDA
Athaliana        FQCELVMAKMGINPIMMSAGELESGNAGEPAKLIRQRYREAADLIKKGKMCCLFINDLDA
Soyshort         FQCELVFAKMGINPIMMSAGELESGNAGEPAKLIRQRYREAADMIKKGKMCALFINDLDA
Soylong          FQCELVFAKMGINPIMMSAGELESGNAGEPAKLIRQRYREAADMIKKGKMCALFINDLDA
Miscanth_short   FQCELVFAKMGIIPIMMSAGELESGNAGEPAKLIRQRYREAADLISKGKMSCLFINDLDA
Miscanth_long    FQCELVFAKMGINPIVMSAGELESGNAGEPAKLIRQRYREAADMIKKGKMCVLFINDLDA
                             ↑135                          ↑163
tobacco          GAGRMGGTTQYTVNNQMVNATLMNIADNPTNVQLPGMYNKQENARVPIIVTGNDFSTLYA
Athaliana        GAGRMGGTTQYTVNNQMVNATLMNIADNPTNVQLPGMYNKEENARVPIICTGNDFSTLYA
Soyshort         GAGRLGGTTQYTVNNQMVNATLMNIADNPTNVQLPGMYNKEENPRVPIIVTGNDFSTLYA
Soylong          GAGRLGGTTQYTVNNQMVNATLMNIADNPTNVQLPGMYNKEENPRVPIIVTGNDFSTLYA
Miscanth_short   GAGRMGGTTQYTVNNQMVNATLMNIADNPTNVQLPGMYNKVDNARVPIIVTGNDFSTLYA
Miscanth_long    GAGRMGGTTQYTVNNQMVNATLMNIADNPTNVQLPGMYNKVDNARVPIIVTGNDFSTLYA tobacco          PLIRDGRMEKFYWAPTREDRIGVCTGIFRTDNVPAEDVVKIVDNFPGQSIDFFGALRARV
Athaliana        PLIRDGRMEKFYWAPTREDRIGVCKGIFRTDKIKDEDIVTLVDQFPGQSIDFFGALRARV
Soyshort         PLIRDGRMEKFYWAPTREDRIGVCTGIFRTDGIPEQDIVKLVDTFPGQSIDFFGALRARV
Soylong          PLIRDGRMEKFYWAPTRDDRVGVCNGIFRTDNVPKDDIVKLVDTFPGQSIDFFGALRARV
Miscanth_short   PLIRDGRMEKFYWAPTREDRIGVCKGIFRTDGVDEEHVVQLVDTFPGQSIDFFGALRARV
Miscanth_long    PLIRDGRMEKFYWAPTREDRVGVCKGIFRTDGVPDEHVVQLVDAFPGQSIDFFGALRARV
                                      ↑262
tobacco          YDDEVRKWVSGTGIEKIGDKLLNSFDGPPTFEQPKMTIEKLLEYGNMLVQEQENVKRVQL
Athaliana        YDDEVRKFVESLGVEKIGKRLVNSREGPPVFEQPEMTYEKLMEYGNMLVMEQENVKRVQL
Soyshort         YDDEVRKWISGVGVDSVGKKLVNSKDGPPTFEQPKMTLEKLLLYGNMLVQEQENVKRVQL
Soylong          YDDEVRKWISVVGVDFIGKKLVNSKEGPPTFDQPKMTLSKLLEYGNMLVQEQENVKRVQL
Miscanth_short   YDDEVRRWVAETGVENIAKKLVNSKDGPPTFEQPKMTIEKLLEYGHMLVAEQENVKRVQL
Miscanth_long    YDDEVRRWVAETGVENIARRLVNSKEGPPTFEQPRMTLDKLMEYGRMLVEEQENVKRVQL tobacco          ADKYLKEAALGDANADAINNGSFFAS-----------------------------------
Athaliana        AETYLSQAALGDANADAIGRGTFYGK--TEV------------------------------
Soyshort         ADKYLNEAALGNANEDAIQRGTFFQS-----------------------------------
Soylong          ADKYLKEAALGDANQDSINRGTFYGKAAQQVNIPVPEGCTDPNASNFDPTARSDDGTCLY
Miscanth_short   ADKYLNEAALGAANEDAMKTGNFFK------------------------------------
Miscanth_long    ADKYLTEAALGDANDDAIIRGDLYGKAAQQVRVPVPEGCTDPKAGNFDPAARSDDGSCVY
                   ↑ AAA+ domain end
tobacco          --
Athaliana        --
Soyshort         --
Soylong          TP
Miscanth_short   --
Miscanth_long    N-
```

FIGURE 2A

| Residue | Replaced by | | | | |
|---|---|---|---|---|---|
| 75 Met | Leu | | | | |
| 85 Met | Leu | | | | |
| 97 Met | Leu | | | | |
| 98 Thr | Ser | | | | |
| 104 Val | Ile | | | | |
| 129 Met | Leu | | | | |
| 135 Met | Leu | Ala | Val | Ile | Arg |
| 136 Met | Leu | Ala | Val | Ile | |
| 163 Met | Ile | Leu | | | |
| 165 Lys | Arg | | | | |
| 169 Met | Leu | | | | |
| 171 Ala | Val | | | | |
| 173 Phe | Leu | | | | |
| 196 Met | Leu | Ala | Val | Thr | Ser |
| 202 Met | Leu | Ala | Val | Thr | Ser |
| 216 Met | Leu | | | | |
| 262 Val | Ile | | | | |
| 264 Thr | Lys | | | | |
| 269 Thr | Ser | | | | |
| 278 Val | Thr | Ile | | | |
| 279 Lys | Arg | Thr | | | |
| 280 Leu | Ile | | | | |
| 310 Gly | Ser | Thr | | | |
| 313 Val | Ala | | | | |
| 315 Ser | Asn | Gly | Ala | Thr | Val |

FIGURE 2B

Soy bean short form mature protein numbering

```
        10         20         30         40         50         60
AVEEKKEIEE TQQTDKDRWK GLAYDISDDQ QDITRGKGLV DSLFQAPQDA GTHYAVMSSY 70         80         90        100        110        120
EYLSTGLRQY LDNKMDGFYI APAFMDKLVV HISKNFMMLP NIKMPLILGI WGGKGQGKSF 130        140        150        160        170        180
QCELVFAKMG INPIMMSAGE LESGNAGEPA KLIRQRYREA ADMIMKGKMC MLMINDLDAG 190        200        210        220        230        240
AGRLGGTTQY TVNNQMVNAT LMNIADNPTN VQLPGMYNKE ENPRVPIIVT GNDFSTLYAP 250        260        270        280        290        300
LIRDGRMEKF YWAPTREDRI GMCMGIFRMD GIPEQDIMM  VDTFPGQSID FFGALRARVY 310        320        330        340        350        360
DDEVRKWISM VGMDMVGKKL VNSKDGPPTF EQPKMTLEKL LLYGNMLVQE QENVKRVQLA 370        380
DKYLNEAALG NANEDAIQRG TFFQS
```

*italic*-sampled positions; bold-differ in long form

SOY-SHORT-AAA⁺ domain sequence (residues 71-362)

```
LDNKMDGFYI APAFMDKLVV HISKNFMMLP NIKMPLILGI WGGKGQGKSF

QCELVFAKMG INPIMMSAGE LESGNAGEPA KLIRQRYREA ADMIMKGKMC MLMINDLDAG

AGRLGGTTQY TVNNQMVNAT LMNIADNPTN VQLPGMYNKE ENPRVPIIVT GNDFSTLYAP

LIRDGRMEKF YWAPTREDRI GMCMGIFRMD GIPEQDIMM  VDTFPGQSID FFGALRARVY

DDEVRKWISM VGMDMVGKKL VNSKDGPPTF EQPKMTLEKL LLYGNMLVQE QENVKRVQLA

ATPase assay AAA+ domain

ATPase assay full-length proteins

Thermofluor assay full-length proteins
(DSF normalized data)

STABILIZATION OF RUBISCO ACTIVASE FOR ENHANCED PHOTOSYNTHESIS AND CROP YIELDS

CROSS REFERENCE TO RELATED APPLICATIONS

This application claims benefit of U.S. Provisional Application No. 62/402,227, filed Sep. 30, 2016, the content of which is hereby incorporated by reference in its entirety.

STATEMENT OF GOVERNMENT SUPPORT

The United States Government claims certain rights in this invention pursuant to Contract No. W-31-109-ENG-38 between the United States Government and the University of Chicago and/or pursuant to DE-AC02-06CH11357 between the United States Government and UChicago Argonne, LLC representing Argonne National Laboratory.

FIELD

The present disclosure relates generally to modified rubisco activase and uses thereof.

SEQUENCE LISTING

The instant application contains a Sequence Listing which has been submitted electronically in ASCII format and is hereby incorporated by reference in its entirety. Said ASCII copy, created on Nov. 10, 2017, is named 051583-0802_SL.txt and is 46,775 bytes in size.

BACKGROUND

Plants are the greatest carbon dioxide sinks on earth. They convert atmospheric $CO_2$ with the help of sunlight into biomass. Plants grow poorly at temperatures even modestly higher than their optimum growth temperature (5-10° C.) utilizing $CO_2$ less efficiently. A recent study reported that global warming (associated with higher $CO_2$ in the atmosphere) already adversely affects harvest yields of food crops such as maize and wheat. Lobell et al. Climate trends and global crop production since 1980. Science, 5 May 2011. DOI: 10.1126/science.1204531. Consequently, heat stable plants are required to maintain food security in light of climate change. Indeed, global average temperatures are expected to rise even further; therefore, it is an essential problem to solve.

Rubisco is an enzyme that catalyzes the first step in carbon fixation utilizing atmospheric $CO_2$ and is found in all photosynthetic bacteria, algae and plants. Rubisco requires another enzyme, rubisco activase, for activation.

While rubisco is a fairly heat stable protein, the rubisco activase is not. It is well established that the inhibition of $CO_2$ assimilation and net photosynthesis (affecting plant growth) is due to thermal instability of rubisco activase. Thus, there exists a need in the art for a heat stable rubisco activase.

SUMMARY

Aspects of the disclosure relate to a modified rubisco activase, wherein the modified rubisco activase has a melting temperature greater than that of wild type rubisco activase. In some embodiments, the modified rubisco activase has a melting temperature greater than about 30.4° C., 34.5° C., 34.9° C., 38.8° C., 39.8° C., 42.8° C., 44.4° C., or 46.0° C. In some embodiments, the rubisco activase has a melting temperature at least about 3, 4, 5, 6, 7, 8, 9, 10, 11, 12, 13, or 14° C. greater than the melting temperature of wild type rubisco activase.

In some embodiments, the modified rubisco activase comprises one or more mutations in the AAA+ domain of the enzyme. In some embodiments, the rubisco activase comprises a point mutation at one or more amino acid positions selected from 135, 163, and 262 based on the sequence of soy β rubisco activase. In some embodiments, the point mutation at amino acid position 135 results in a substitution of R for the naturally occurring amino acid at this position, the point mutation at amino acid position 163 results in a substitution of I for the naturally occurring amino acid at this position, and/or the point mutation at amino acid position 262 results in a substitution of I for the naturally occurring amino acid at this position. In some embodiments, the modified rubisco activase comprises point mutations at one, two, or all three amino acid positions.

In some embodiments, the rubisco activase is soy β rubisco activase. In further embodiments, the rubisco activase comprises one or more point mutations selected from M135R, M163I, and V262I. In some embodiments, the modified rubisco activase comprises one, two, or all three of these point mutations. In some embodiments, the modified rubisco activase comprises point mutations at M135R, M163I, and V262I.

In some embodiments, the rubisco activase is *Miscanthus* β rubisco activase. In further embodiments, the rubisco activase comprises one or more point mutations selected from M133R, L161I, and V260I based on the sequence of *Miscanthus* β rubisco activase. In some embodiments, the modified rubisco activase comprises one, two, or all three of these point mutations. In some embodiments, the modified rubisco activase comprises point mutations at M133R, L161I, and V260I.

Further aspects of the disclosure relate to an isolated polynucleotide encoding a modified rubisco activase disclosed herein and a recombinant expression system comprising the isolated polynucleotide. Still further aspects of the disclosure relate to a plant cell transfected with the recombinant expression system.

Certain aspects of the disclosure relate to a genetically modified plant expressing the isolated polynucleotide encoding a modified rubisco activase disclosed herein. In some embodiments, the genetically modified plant is a genetically modified *Arabidospis*, soybean, or *Miscanthus giganteus* plant.

BRIEF DESCRIPTION OF DRAWINGS

FIG. 1 is a sequence alignment (SEQ ID NOS 25-30, respectively, in order of appearance) showing highly conserved sequence across multiple species of rubisco activase.

FIG. 2A is a table of mutations made to the AAA+ domain of soy β rubisco activase. FIG. 2B shows the sequence of soy β rubisco activase and the positions at which modifications were made (SEQ ID NOS 27 and 31, respectively, in order of appearance).

FIG. 3 is the DNA sequence of soy β rubisco activase (SEQ ID NO: 32), optimized for expression in *E. coli* (SEQ ID NO: 27).

DETAILED DESCRIPTION

Figure 4A:
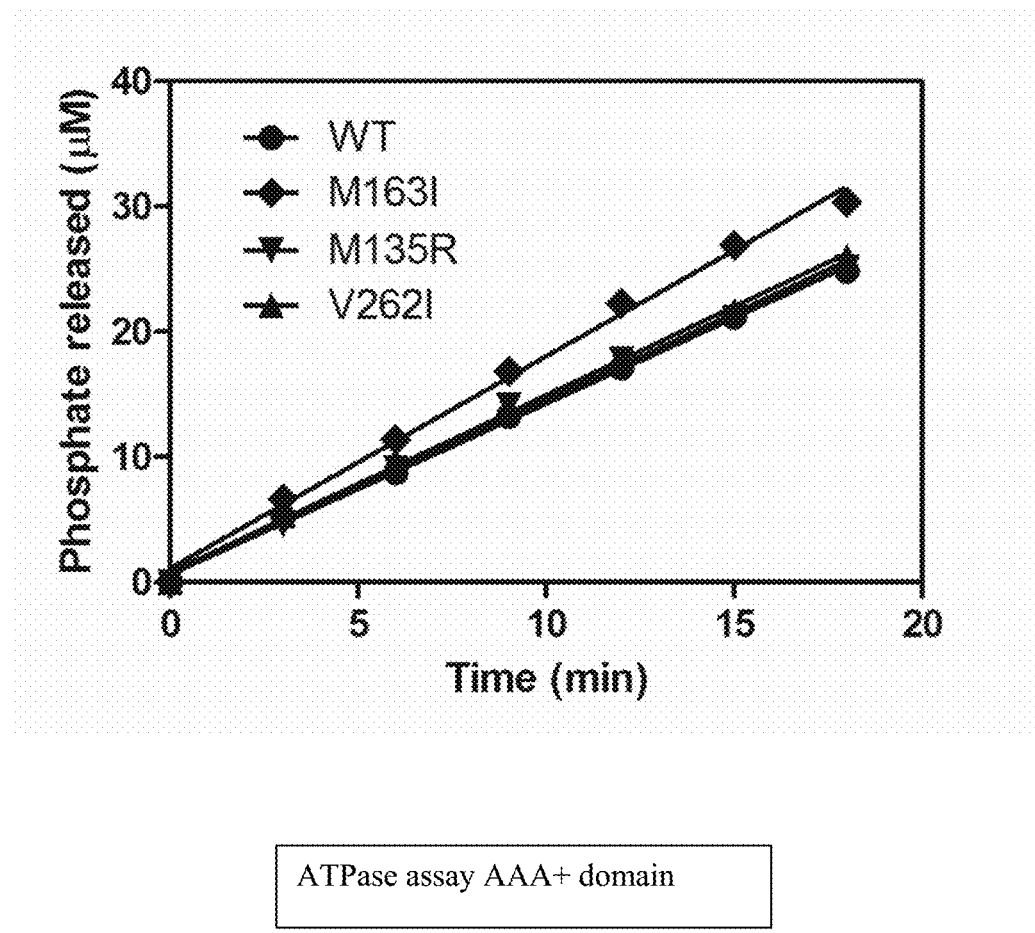
FIG. 4A shows the results of the an ATP hydrolysis assay for wild-type and three mutant AAA+ domains of soy β rubisco activase.

Unless defined otherwise, all technical and scientific terms used herein have the same meanings as commonly understood by one of ordinary skill in the art to which this disclosure belongs. All nucleotide sequences provided herein are presented in the 5' to 3' direction. Although any methods and materials similar or equivalent to those described herein can be used in the practice or testing of the present disclosure, particular, non-limiting exemplary methods, devices, and materials are now described. All technical and patent publications cited herein are incorporated herein by reference in their entirety. Nothing herein is to be construed as an admission that the disclosure is not entitled to antedate such disclosure by virtue of prior invention.

The practice of the present disclosure will employ, unless otherwise indicated, conventional techniques of tissue culture, immunology, molecular biology, microbiology, cell biology and recombinant DNA, which are within the skill of the art. See, e.g., Green and Sambrook eds. (2012) Molecular Cloning: A Laboratory Manual, 4th edition; the series Ausubel et al. eds. (2015) Current Protocols in Molecular Biology; the series Methods in Enzymology (Academic Press, Inc., N.Y.); MacPherson et al. (2015) PCR 1: A Practical Approach (IRL Press at Oxford University Press); MacPherson et al. (1995) PCR 2: A Practical Approach; McPherson et al. (2006) PCR: The Basics (Garland Science); Harlow and Lane eds. (1999) Antibodies, A Laboratory Manual; Greenfield ed. (2014) Antibodies, A Laboratory Manual; Freshney (2010) Culture of Animal Cells: A Manual of Basic Technique, 6th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Herdewijn ed. (2005) Oligonucleotide Synthesis: Methods and Applications; Hames and Higgins eds. (1984) Transcription and Translation; Buzdin and Lukyanov ed. (2007) Nucleic Acids Hybridization: Modern Applications; Immobilized Cells and Enzymes (IRL Press (1986)); Grandi ed. (2007) In Vitro Transcription and Translation Protocols, 2nd edition; Guisan ed. (2006) Immobilization of Enzymes and Cells; Perbal (1988) A Practical Guide to Molecular Cloning, 2nd edition; Miller and Calos eds, (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Lundblad and Macdonald eds. (2010) Handbook of Biochemistry and Molecular Biology, 4th edition; and Herzenberg et al. eds (1996) Weir's Handbook of Experimental Immunology, 5th edition.

All numerical designations, e.g., pH, temperature, time, concentration, and molecular weight, including ranges, are approximations which are varied (+) or (−) by increments of 1.0 or 0.1, as appropriate or alternatively by a variation of +/−15%, or alternatively 10% or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

DEFINITIONS

As used in the specification and claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions disclosed herein. Embodiments defined by each of these transition terms are within the scope of this disclosure.

The term "protein", "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. The term "enzyme" as used herein refers to a specific type of protein that serves as a catalyst for a particular reaction.

A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics. The amino acids may be numbered based on a reference sequence to designate their position in the protein or peptide.

As used herein the term "amino acid" refers to either natural and/or unnatural or synthetic amino acids, including, but not limited to, the twenty commonly occurring amino acids alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V) and both the D or L optical isomers thereof, and amino acid analogs and peptidomimetics. The term "amino acid" is used herein in the conventional sense to refer to organic chemical moieties which comprise an amino group ($-NH_2$) and a carboxylic acid group ($-COOH$). Amino acids may be further grouped based on their side chains, e.g. "hydrophobic amino acids" are those with hydrophobic side chains, including, but not limited to, alanine (A), isoleucine (I), leucine (L), valine (V), phenylalanine (F), tryptophan (W) or tyrosine (Y) and "hydrophilic amino acids" are those with charged or polar side chains, including, but not limited to, arginine (R), asparagine (N), aspartic acid (D), glutamine (Q), glutamic acid (E), histidine (H), lysine (K), serine (S), and threonine (T).

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment disclosed herein that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, fragment, polypeptide or nucleic acid, intends those having minimal homology while still maintaining desired structure or functionality. Unless specifically recited herein, it is contemplated that any polynucleotide, polypeptide or protein mentioned herein also includes equivalents thereof. In one aspect, an equivalent polynucleotide is one that hybridizes under stringent conditions to the polynucleotide or complement of the polynucleotide as described herein for use in the described methods. In another aspect, an equivalent antibody or antigen binding polypeptide intends one that binds with at least 70%, or alternatively at least 75%, or alternatively at least 80%, or alternatively at least 85%, or alternatively at least 90%, or alternatively at least 95% affinity or higher affinity to a reference antibody or antigen binding fragment. In another aspect, the equivalent thereof competes with the binding of the antibody or antigen binding fragment to its antigen tinder a competitive ELISA assay. In another aspect, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art. In certain embodiments, default parameters are used for alignment. A non-limiting exemplary alignment program is BLAST, using default parameters. In particular, exemplary programs include BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. Sequence identity and percent identity were determined by incorporating them into clustalW (available at the web address: genome.jp, Bioinformatics Tools, last accessed on Jul. 14, 2016).

As used herein the term "modified" used to describe a protein that differs from the isolated wild type protein in at least one aspect: that it is produced artificially, e.g. through recombinant expression, mutagenesis, etc. A modified protein may comprise one or more mutations. Suitable mutations include insertions, deletions, substitutions, and/or frameshifts in the amino acid sequence of the protein. The term "point mutation" as used herein refers to a substitution at a single amino acid position in the amino acid sequence of the protein. A modified protein may comprise one or more point mutations.

The term "recombinant expression system" as used herein refers to a construct or vector designed to allow gene expression of a protein or peptide in a host cell. Recombinant expression systems generally employ a bacterial plasmid or viral vector. In addition to the gene to be expressed, such expression systems may comprise one or more regulatory polynucleotide sequences such as enhancers, inducers, or promoters that control the expression of the protein or peptide. Alternatively or in addition, such expression systems may comprise one or more detectable labels to assist in the purification of the protein or peptide. The appropriate recombinant expression system may be selected depending on the host cell, e.g. pMCSG81 for expression in *E. coli*. Further tags and/or other detectable labels (cleavable or non-cleavable) may be used at the C-terminus or N-terminus of the protein being expressed, e.g. a non-cleavable His₆ tag (SEQ ID NO: 33) at the C-terminus of the protein being expressed.

The term "plant" as used herein refers to a multicellular eukaryote of the kingdom Plantae. A "plant cell" refers to cells characteristically found in plants characterized by the presence of a cell wall comprising cellulose and the presence of plastids, e.g. choloroplasts. The term "genetically modified" is used to describe a plant whose genetic material has been artificially altered, e.g. by transfection of a recombinant expression system into one or more of its cells, mutagenesis, etc.

Modes of Carrying Out the Disclosure

The present disclosure relates generally to a modified rubisco activase. Rubisco activase is an enzyme found in plants that is responsible for the activation of rubisco—the first enzyme in the carbon fixation pathway of photosynthesis in plants.

The sequence of rubisco activase for a variety of plant species, e.g. C6T859 (>gi|290766491|gb|ADD60248.1| beta-form rubisco activase [*Glycine max*]). The AAA+ domain houses its ATP hydrolysis function. See Stotz M. et al. Structure of green-type Rubisco activase from tobacoo. Nature Str Mol Biol. 18:1366-70 (2011). The canoncial sequence of soy β rubisco activase is:

(SEQ ID NO: 1)
MAASVSTVGAVNRALLNLNGSGAGASAPSSAFFGTSLKKVIASRVPNSKV

SGGSFKIVAVEEKKEIEETQQTDKDRWKGLAYDISDDQQDITRGKGLVDS

LFQAPQDAGTHYAVMSSYEYLSTGLRQYLDNKMDGFYIAPAFMDKLVVHI

SKNFMTLPNIKVPLILGIWGGKGQGKSFQCELVFAKMGINPINMSAGELE

SGNAGEPAKLIRQRYREAADMIKKGKMCALFINDLDAGAGRLGGTTQYTV

NNQMVNATLMNIADNPTNVQLPGMYNKEENPRVPIIVIGNDFSTLYAPLI

RDGRMEKEYWAPTREDRIGVCTGIFRTDGIPEQDIVKLVDTFPGQSIDFF

GALRARVYDDEVRKWISGVGVDSVGKKLVNSKDGPPTFEQPKMTLEKLLL

YGNMLVQEQENVKRVQLADKYLNEAALGNANEDAIQRGTFFQS

The italicized, underlined segment above is the chloroplast transit peptide, which is removed in the mature protein sequence. The amino acid numbering referred to herein corresponds to the mature protein sequence (without the chloroplast transit peptide).

The bolded, underlined segment above is the AAA+ domain of this enzyme. The AAA+ domain is defined as amino acids 68-360 in *Arabidopsis thaliana*. See FIG. 1a of Stotz et al. Structure of green-type Rubisco activase from tobacco. Nat. Struct. Mol. Biol. 18, 1366-70 (2011). The equivalent AAA+ domain in soybean β rubisco activase is amino acids 71-362 of the mature protein sequence (without the chloroplast transit peptide) underlined above.

In some embodiments, the modified rubisco activase comprises one or more mutations in the AAA+ domain of the enzyme. In some embodiments, the rubisco activase comprises a point mutation at one or more amino acid positions selected from 135, 163, and 262 based on the soy β rubisco activase sequence provided herein above. In some embodiments, the modified rubisco activase comprises point mutations at one, two, or all three amino acid positions. In some embodiments, the rubisco activase comprises one or more point mutations selected from M135R, M163I, and V262I. FIG. 3 provides the DNA sequence for the soy β rubisco activase optimized for expression in *E. coli*; mutations in the underlying DNA sequence can result in the mutant proteins. For example, an M135R mutant results from an ATG to CGG codon change; an M163I mutant results from an ATG to ATC codon change, and a V262I mutant results from an GTG to ATC codon change. Not to be bound by theory, these mutants are hypothesized to affect certain changes to the rubisco activase enzyme, e.g. V262I may optimize the internal packing of side chains; M163I may optimize the internal packing and/or reduce side chain entropy; M135R may form a salt bridge with E121. In some embodiments, the modified rubisco activase comprises one, two, or all three of these point mutations.

The positions of mutations in the soy β rubisco activase disclosed herein can be used to determine suitable point mutation sites in other rubisco activase. For example, the canonical sequence of the corresponding protein in *Miscanthus giganteus* ("*Miscanthus* β rubisco activase") is:

(SEQ ID NO: 2)
MAAAFSSTVGAPASTPSRSSFLGKKLNKQQVSAAAVNYHGKSSSSAANRF

KVMAAKEVDETKETDGDRWKGLAFDISDDQQDITRGKGMIDSLFQAPMGD

GTHVAVLSSYDYISQGQKTYSMDNTMDGFYIARGFMDKLVVHLSKNFMKL

PNIKVPLILGIWGGKGQGKSFQCELVFAKMGIIPIMMSAGELESGNAGEP

AKLIRQRYREAADLISKGEMSCLFINDLDAGAGRMGGTTQYTVNNQMVNA

TLMNIADNPTNVQLPGMYNKVDNARVPIIVTGNDFSTLYAPLIRDGRMEK

FYWAPTREDRIGVCKGIFRTDGVDEEHVVQLVDTFPGQSIDFFGALRARV

YDDEVRRWVAETGVENIAKKLVNSKDGPPTFEQPKMTIEKLLEYGHMLVA

EQENVKRVQLADKYLNEAALGAANEDAMKTGNFFK

As with the soybean β rubisco activase sequence, the italicized, underlined segment above is the chloroplast transit peptide, which is removed in the mature protein sequence. The amino acid numbering referred to herein corresponds to the mature protein sequence (without the chloroplast transit peptide). The bolded, underlined segment above is the AAA+ domain of this enzyme.

The corresponding *Miscanthus* protein can be modified to have a point mutation at one or more amino acid positions selected from 135, 163, and 262 based on the soy β rubisco activase sequence provided herein above. Based on alignment to soy β rubisco activase (FIG. 1), these mutations fall at amino acid positions 133, 161, and 260 in the corresponding *Miscanthus* protein. Thus, the point mutations M135R, M163I, and V262I based on the soy β rubisco activase sequence are equivalent to point mutations M133R, L161I, and V260I in corresponding *Miscanthus* protein.

In both cases, the sequence numbers for the point mutations were determined from the N-terminal residue of each mature protein (i.e., chloroplast transit peptide sequence deleted). The numbers vary slightly because of differences in the N-terminal residues between soy β rubisco activase and the corresponding *Miscanthus* protein. The corresponding mutations in other rubisco activase sequences, including but not limited to those listed in FIG. 1, may be determined by alignment in the same or similar manner.

Aspects of the disclosure relate to a modified rubisco activase with a melting temperature greater than that of wild type rubisco activase; thus, a heat-stable rubisco activase.

Melting temperature can be measured thermofluor assay (also referred to as Differential Scanning Fluorimetry assay) using Sypro orange dye. See Vedadi et al. Chemical screening methods to identify ligands that promote protein stability, protein crystallization, and structure determination. PNAS, 103, 15835-15840 (2006); Niesen et al. The use of differential scanning fluorimetry to detect ligand interactions that promote protein stability. Nat Protoc. 2, 2212-21 (2007).

In some embodiments, the modified rubisco activase has a melting temperature greater than about 30.4° C., 34.5° C., 34.9° C., 38.8° C., 39.8° C., 42.8° C., 44.4° C., or 46.0° C. In some embodiments, the rubisco activase has a melting temperature at least about 3, 4, 5, 6, 7, 8, 9, 10, 11, 12, 13, or 14° C. greater than the melting temperature of wild type rubisco activase.

Further aspects of the disclosure relate to an isolated polynucleotide encoding a modified rubisco activase disclosed herein. Methods of determining the isolated polynucleotide sequence of a given protein or peptide are well understood.

The isolated polynucleotide may be comprised in a recombinant expression system. In some embodiments, the recombinant expression system may be codon optimized or otherwise altered to enhance expression, e.g. through the inclusion of one or more regulatory polynucleotide sequences.

A non-limiting exemplary expression system may be pMCSG81 (vector).

A plant cell may be transfected with the recombinant expression system. Techniques for transfection of recombinant expression system are selected based on the host cell used. Non-limiting exemplary methods of transfection tailored to plant cells include using a bacterial or viral vector (e.g. via *Agrobacterium tumefaciens* transfection, described in Kurek et al. The Plant Cell (2007) 19:3230-3241).

Certain aspects of the disclosure relate to a genetically modified plant expressing the isolated polynucleotide encoding a modified rubisco activase disclosed herein. Non-limiting examples of plants that may be genetically modified include: *Arabidospis*, soybean, *Miscanthus giganteus* plant, and those plants with rubisco activase sequences listed in FIG. 1. Genetic modification of these plants may be accomplished through any one of the following non-limiting exemplary techniques CRISPR-CAS9 and TALEN.

Example 1—Generation of Heat-Stable Modified Rubisco Activase

Soybean β Rubisco Activase AAA+ domain was first cloned in a vector and amino acid substitutions were performed using standard mutagenesis methods. (QuikChange site directed mutagenesis kits from Agilent Technologies). Primers used in this process are provided herein below:

```
Primers for cloning into pMCSG81
(with C-term His-Tag, non-cleavable):
p81SS-F
GGAGTAAAGATAATGGCAGTGGAGGAGAAAAAAGAGATTGAAG (SEQ ID NO: 3)

p81SS-R
GTGATGGTGATGATGTGATTGAAAGAATGTGCCACGTTGGATT (SEQ ID NO: 4)

p81SSAAA-F
GGAGTAAAGATAATGCTGGATAACAAAATGGATGGTTTTTACATTGCT (SEQ ID NO: 5)

p81SSAAA-R
GTGATGGTGATGATGTTTATCTGCCAGTTGCACGCGTTTAACA (SEQ ID NO: 6)

Mutagenic Primers for constructing site-directed
mutants: Target codon is underlined and base
changes are bolded and italicized (in forward primer)

M135RF
GGG TAT CAA TCC AAT TCG GAT GAG TGC TGG AGA ACT CG (SEQ ID NO: 7)

M135RR
CGA GTT CTC CAG CAC TCA TCC GAA TTG GAT TGA TAC CC (SEQ ID NO: 8)

M163IF
CCG GGA AGC AGC CGA TAT CAT TAA GAA AGG AAA AAT G (SEQ ID NO: 9)

M163IR
CAT TTT TCC TTT CTT AAT GAT ATC GGC TGC TTC CCG G (SEQ ID NO: 10)

V262IF
CGT GAA GAT CGT ATT GGT
ATC TGT ACA GGT ATT TTC CGC AC (SEQ ID NO: 11)

V262IR
GTG CGG AAA ATA CCT GTA CAG ATA CCA ATA CGA TCT TCA CG
(SEQ ID NO: 12)
```

A total of 48 full length soybean β rubisco activase mutants were generated and analyzed for heat stability relative to wild type full length soybean β rubisco activase.

Figure 4B:
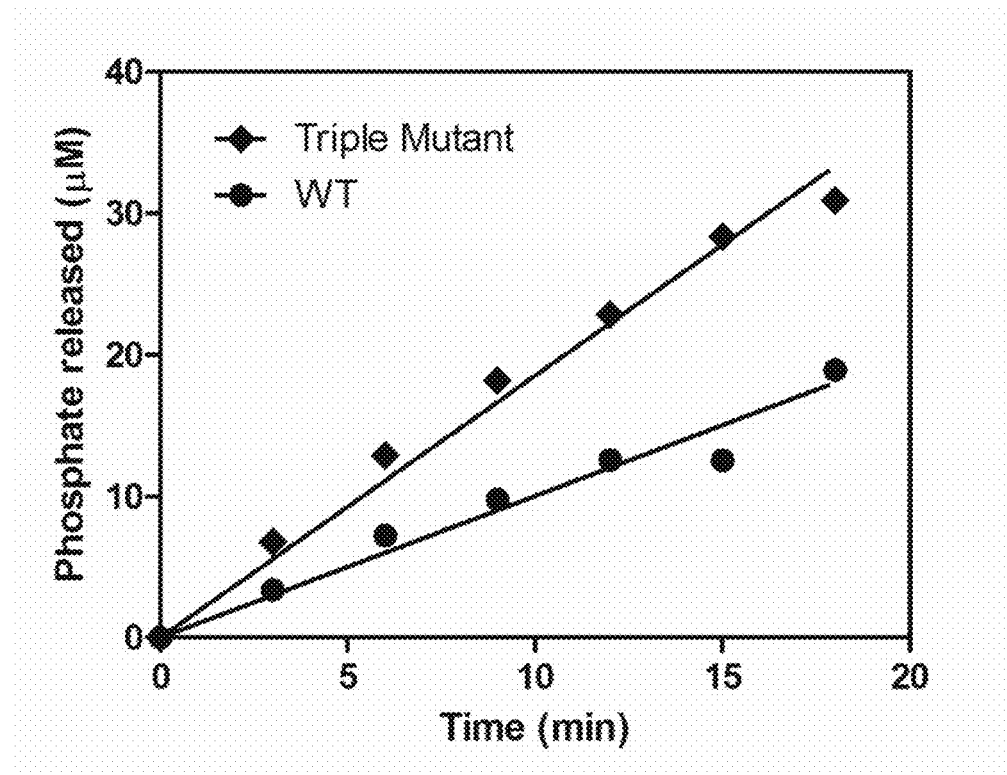
FIG. 4B shows the results of an ATP hydrolysis assay for wild-type and triple mutant of soy β rubisco activase.
Figure 4C:
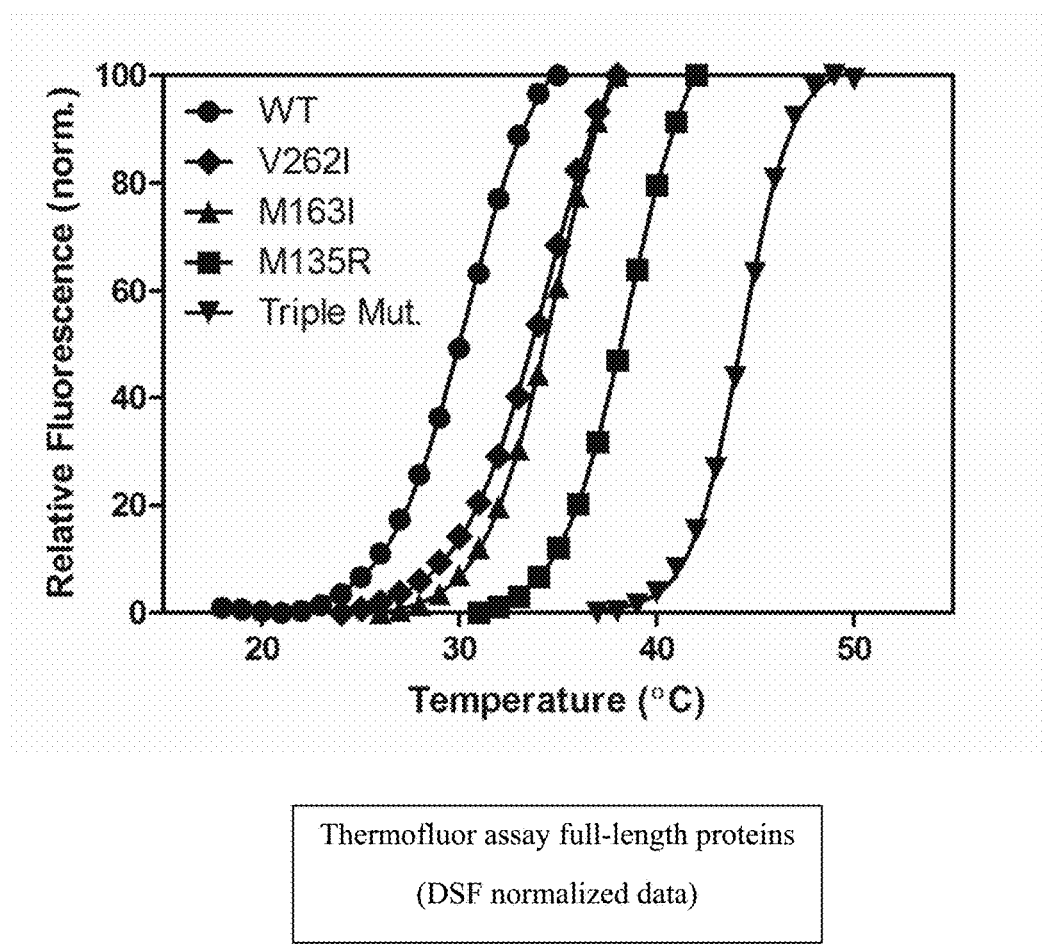
FIG. 4C shows the thermostability assay for wild-type, single stability mutants and the triple mutant of soy β rubisco activase.

Three individual mutants, each comprising a single point mutation, demonstrated melting temperature increases between 4.1-8.4° C. relative to wild type rubisco activase (Table 1). Further, a triple mutant comprising all three point mutations had a melting temperature increase of 14° C. (Table 1; FIG. 4C).

TABLE 1

| Protein | Tm (° C.) | ΔTm (° C.) |
| --- | --- | --- |
| WT | 30.4 | — |
| M135R | 38.8 | 8.4 |
| M163I | 34.9 | 4.5 |
| V262I | 34.5 | 4.1 |
| Triple mutant | 44.4 | 14 |

Rubisco activase from *Miscanthus giganteus* was cloned and expressed with the intention of transferring the stability mutations observed in the soybean rubisco activase. The *Miscanthus* β rubisco activase (short form) was produced as both the full-length protein and the corresponding AAA+ domain, as described for the soybean rubisco activase. Not to be bound by theory, the *Miscanthus* β rubisco activase is believed to have a higher stability compared to the corresponding soybean protein. The candidate stability mutants in the *Miscanthus* sequence are M133R, L161I and V260I. These mutations were incorporated using site-directed mutagenesis and the melting temperatures were assessed.

The *Miscanthus* β rubisco activase (short form), codon optimized (stop codon in lower case) nucleic acid sequence is:

```
(SEQ ID NO: 13)
GCAGCCAAAGAAGTGGACGAAACAAAAGAAACTGATGGTGATCGTTGGAA

AGGCCTTGCGTTTGATATTAGTGATGACCAACAAGATATTACTCGTGGTA

AAGGCATGATTGATTCTTTATTTCAAGCACCTATGGGTGACGGAACGCAC

GTTGCAGTTTTATCTTCTTACGATTATATTTCCCAAGGTCAAAAAACATA

TTCAATGGATAATACTATGGACGGCTTTTATATTGCGCGCGGTTTTATGG

ATAAACTCGTGGTTCATCTCAGCAAAAATTTTATGAAACTTCCAAACATT

AAAGTACCGTTAATCCTGGGCATTTGGGGAGGAAAAGGTCAAGGCAAATC

ATTTCAATGTGAATTAGTATTTGCGAAAATGGGGATTATTCCAATTATGA

TGTCTGCAGGCGAATTAGAAAGCGGGAATGCGGGCGAACCAGCTAAACTT

ATCCGTCAGCGTTATCGTGAAGCGGCTGATTTAATCTCAAAAGGCAAAAT

GTCGTGTCTCTTTATCAATGATTTAGATGCGGGCGCTGGACGTATGGGCG

GGACGACTCAATATACTGTTAACAATCAAATGGTGAACGCTACCCTGATG

AATATTGCTGATAACCCTACGAATGTACAATTACCTGGCATGTATAACAA

AGTTGATAACGCACGCGTACCGATTATTGTCACTGGTAACGATTTTAGCA

CCCTTTACGCACCCCTTATTCGTGACGGTCGCATGGAAAAATTTTATTGG

GCACCAACTCGGGAGGATCGCATCGGAGTTTGTAAAGGCATTTTTCGGAC

TGATGGTGTTGATGAGGAACATGTTGTGCAATTAGTGGATACGTTCCCTG

GTCAAAGTATTGATTTCTTCGGCGCCTCCGCGCTCGTGTGTATGACGAC

GAAGTACGCCGCTGGGTCGCAGAAACTGGTGTTGAAAATATCGCCAAAAA

ATTAGTAAATTCCAAAGACGGCCCCCCTACTTTCGAACAACCTAAAATGA

CTATTGAAAAATTATTAGAATATGGTCACATGCTGGTAGCAGAACAAGAA

AACGTTAAACGCGTACAACTTGCCGATAAATACTTGAATGAAGCAGCACT

TGGAGCAGCTAACGAAGATGCGATGAAAACTGGAAATTTTTTTAAAtaa
```

The corresponding amino acid sequence is:

```
(SEQ ID NO: 14)
AAKEVDETKETDGDRWKGLAFDISDDQQDITRGKGMIDSLFQAPMGDGT

HVAVLSSYDYISQGQKTYSMDNTMDGFYIARGFMDKLVVHLSKNFMKLP

NIKVPLILGIWGGKGQGKSFQCELVFAKMGIIPIMMSAGELESGNAGEP

AKLIRQRYREAADLISKGKMSCLFINDLDAGAGRMGGITQYTVNNQMVN

ATLMNIADNPINVQLPGMYNKVDNARVPIIVTGNDFSTLYAPLIRDGRM

EKFYWAPTREDRIGVCKGIFRTDGVDEEHVVQLVDTFPGQSIDFFGALR

ARVYDDEVRRWVAETGVENIAKKLVNSKDGPPTFEQPKMTIEKLLEYGH

MLVAEQENVKRVQLADKYLNEAALGAANEDAMKTGNEFK
```

The following primers were used for cloning this sequence into pMCSG81:

```
38551_Full_p81-F
GGAGTAAAGATAATGGCAGCCAAAGAAGTGGACGAAACAAAA
(SEQ ID NO: 15)

38551_AAA_p81-F
GGAGTAAAGATAATGTCAATGGATAATACTATGGACGGCTTTTATATTG
(SEQ ID NO: 16)

38551_Full_p81-R
GTGATGGTGATGATGTTTAAAAAAATTTCCAGTTTTCATCGCATCTTCG
TTA (SEQ ID NO: 17)

38551_AAA_p81-R
GTGATGGTGATGATGTTTATCGGCAAGTTGTACGCGTTTAACG
(SEQ ID NO: 18)
```

The mutations corresponding to those in soybean β rubisco activase were determined by aligning the sequences (FIG. 1).

Mutagensis was accomplished using the following primers to introduce the stability mutations. The capitalized bases are those base changes required to change the corresponding amino acid.

```
Forward primers:
M133R(F)
ggggattattccaattCGgatgtctgcaggcgaattag
(SEQ ID NO: 19)

L161I(F)
cgttatcgtgaagcggctgatAtCatctcaaaaggcaaaatgtc
(SEQ ID NO: 20)

V260I(F)
ggaggatcgcatcggaAtttgtaaaggcatttttcgg
(SEQ ID NO: 21)

Reverse primers:
M133R(R)
ctaattcgcctgcagacatcCGaattggaataatcccc
(SEQ ID NO: 22)

L161I(R)
gacattttgcctttgagatGaTatcagccgcttcacgataacg
(SEQ ID NO: 23)

V260I(R)
ccgaaaaatgcctttacaaaTtccgatgcgatcctcc
(SEQ ID NO: 24)
```

The melting temperature was measured using Differential Scanning Flourimetry (Thermofluor assay) on small scale protein isolated and partially purified using Ni2+ bead sand are shown in the Table 2 below.

TABLE 2

| Protein | Tm (° C.) | ΔTm (° C.) |
|---|---|---|
| WT | 39.8 | — |
| M133R | 44.0 | 4.2 |
| L161I | — | — |
| V260I | 42.8 | 3.0 |
| Triple mutant | 46.0 | 6.2 |

Example 2—Production of Modified Rubisco Activase and Assessment

Modified rubisco activases of Table 1 are produced using a recombinant expression system.

The proteins were subjected to ATP hydrolysis activity assay, which measures the ATP hydrolysis part of the rubisco activase function. Without the ATP hydrolysis activity, rubisco activase cannot activate rubisco; thus, successful ATP hydrolysis indicates that the ATP hydrolysis part of rubisco activase function is maintained by the mutants (FIG. 4A and FIG. 4B).

This is repeated for the rubisco activases of Table 2 and the stability mutants for *Miscanthus*.

Rubisco activase assay (e.g. Barta et al. (2011) Chapter 29, *Photosynthesis Research Protocols*, Methods in Molecular Biology, vol. 684, DOI 10.1007/978-1-60761-925-3_29; Scales et al. Photosynth Res (2014) 119:355-365, DOI 10.1007/s11120-013-9964-5) is carried out to assess rubisco activase function.

Example 3—Assessment of Modified Rubisco Activase Effect on Plant Growth

Rubisco activase is transfected into *A. thaliana* and tobacco and assessed for its effect on plant growth. See, generally, Kurek et al. The Plant Cell (2007) 19:3230-3241. The plant growth characteristics of plants transfected with wild type rubisco activase versus the stability mutants are compared.

SEQUENCE LISTING

<160> NUMBER OF SEQ ID NOS: 33

<210> SEQ ID NO 1
<211> LENGTH: 443
<212> TYPE: PRT
<213> ORGANISM: Glycine max

<400> SEQUENCE: 1

Met Ala Ala Ser Val Ser Thr Val Gly Ala Val Asn Arg Ala Leu Leu
1               5                   10                  15

Asn Leu Asn Gly Ser Gly Ala Gly Ala Ser Ala Pro Ser Ser Ala Phe
            20                  25                  30

Phe Gly Thr Ser Leu Lys Lys Val Ile Ala Ser Arg Val Pro Asn Ser
        35                  40                  45

Lys Val Ser Gly Gly Ser Phe Lys Ile Val Ala Val Glu Glu Lys Lys
    50                  55                  60

Glu Ile Glu Glu Thr Gln Gln Thr Asp Lys Asp Arg Trp Lys Gly Leu
65                  70                  75                  80

Ala Tyr Asp Ile Ser Asp Asp Gln Gln Asp Ile Thr Arg Gly Lys Gly
                85                  90                  95

Leu Val Asp Ser Leu Phe Gln Ala Pro Gln Asp Ala Gly Thr His Tyr
            100                 105                 110

Ala Val Met Ser Ser Tyr Glu Tyr Leu Ser Thr Gly Leu Arg Gln Tyr
        115                 120                 125

Leu Asp Asn Lys Met Asp Gly Phe Tyr Ile Ala Pro Ala Phe Met Asp
    130                 135                 140

Lys Leu Val Val His Ile Ser Lys Asn Phe Met Thr Leu Pro Asn Ile
145                 150                 155                 160

Lys Val Pro Leu Ile Leu Gly Ile Trp Gly Gly Lys Gly Gln Gly Lys
                165                 170                 175

Ser Phe Gln Cys Glu Leu Val Phe Ala Lys Met Gly Ile Asn Pro Ile
            180                 185                 190

Met Met Ser Ala Gly Glu Leu Glu Ser Gly Asn Ala Gly Glu Pro Ala
        195                 200                 205

Lys Leu Ile Arg Gln Arg Tyr Arg Glu Ala Ala Asp Met Ile Lys Lys
    210                 215                 220

Gly Lys Met Cys Ala Leu Phe Ile Asn Asp Leu Asp Ala Gly Ala Gly

```
                225                 230                 235                 240
Arg Leu Gly Gly Thr Thr Gln Tyr Thr Val Asn Asn Gln Met Val Asn
                245                 250                 255

Ala Thr Leu Met Asn Ile Ala Asp Asn Pro Thr Asn Val Gln Leu Pro
                260                 265                 270

Gly Met Tyr Asn Lys Glu Glu Asn Pro Arg Val Pro Ile Ile Val Thr
                275                 280                 285

Gly Asn Asp Phe Ser Thr Leu Tyr Ala Pro Leu Ile Arg Asp Gly Arg
                290                 295                 300

Met Glu Lys Phe Tyr Trp Ala Pro Thr Arg Glu Asp Arg Ile Gly Val
305                 310                 315                 320

Cys Thr Gly Ile Phe Arg Thr Asp Gly Ile Pro Glu Gln Asp Ile Val
                325                 330                 335

Lys Leu Val Asp Thr Phe Pro Gly Gln Ser Ile Asp Phe Phe Gly Ala
                340                 345                 350

Leu Arg Ala Arg Val Tyr Asp Asp Glu Val Arg Lys Trp Ile Ser Gly
                355                 360                 365

Val Gly Val Asp Ser Val Gly Lys Lys Leu Val Asn Ser Lys Asp Gly
                370                 375                 380

Pro Pro Thr Phe Glu Gln Pro Lys Met Thr Leu Glu Lys Leu Leu Leu
385                 390                 395                 400

Tyr Gly Asn Met Leu Val Gln Glu Gln Glu Asn Val Lys Arg Val Gln
                405                 410                 415

Leu Ala Asp Lys Tyr Leu Asn Glu Ala Ala Leu Gly Asn Ala Asn Glu
                420                 425                 430

Asp Ala Ile Gln Arg Gly Thr Phe Phe Gln Ser
                435                 440

<210> SEQ ID NO 2
<211> LENGTH: 435
<212> TYPE: PRT
<213> ORGANISM: Miscanthus giganteus

<400> SEQUENCE: 2

Met Ala Ala Ala Phe Ser Ser Thr Val Gly Ala Pro Ser Thr Pro
1               5                   10                  15

Ser Arg Ser Ser Phe Leu Gly Lys Lys Leu Asn Lys Gln Gln Val Ser
                20                  25                  30

Ala Ala Ala Val Asn Tyr His Gly Lys Ser Ser Ser Ala Ala Asn
                35                  40                  45

Arg Phe Lys Val Met Ala Ala Lys Glu Val Asp Glu Thr Lys Glu Thr
            50                  55                  60

Asp Gly Asp Arg Trp Lys Gly Leu Ala Phe Asp Ile Ser Asp Gln
65                  70                  75                  80

Gln Asp Ile Thr Arg Gly Lys Gly Met Ile Asp Ser Leu Phe Gln Ala
                85                  90                  95

Pro Met Gly Asp Gly Thr His Val Ala Val Leu Ser Ser Tyr Asp Tyr
                100                 105                 110

Ile Ser Gln Gly Gln Lys Thr Tyr Ser Met Asp Asn Thr Met Asp Gly
                115                 120                 125

Phe Tyr Ile Ala Arg Gly Phe Met Asp Lys Leu Val Val His Leu Ser
            130                 135                 140

Lys Asn Phe Met Lys Leu Pro Asn Ile Lys Val Pro Leu Ile Leu Gly
145                 150                 155                 160
```

```
Ile Trp Gly Gly Lys Gly Gln Gly Lys Ser Phe Gln Cys Glu Leu Val
            165                 170                 175
Phe Ala Lys Met Gly Ile Ile Pro Ile Met Met Ser Ala Gly Glu Leu
        180                 185                 190
Glu Ser Gly Asn Ala Gly Glu Pro Ala Lys Leu Ile Arg Gln Arg Tyr
    195                 200                 205
Arg Glu Ala Ala Asp Leu Ile Ser Lys Gly Lys Met Ser Cys Leu Phe
210                 215                 220
Ile Asn Asp Leu Asp Ala Gly Ala Gly Arg Met Gly Gly Thr Thr Gln
225                 230                 235                 240
Tyr Thr Val Asn Gln Met Val Asn Ala Thr Leu Met Asn Ile Ala
            245                 250                 255
Asp Asn Pro Thr Asn Val Gln Leu Pro Gly Met Tyr Asn Lys Val Asp
        260                 265                 270
Asn Ala Arg Val Pro Ile Ile Val Thr Gly Asn Asp Phe Ser Thr Leu
    275                 280                 285
Tyr Ala Pro Leu Ile Arg Asp Gly Arg Met Glu Lys Phe Tyr Trp Ala
290                 295                 300
Pro Thr Arg Glu Asp Arg Ile Gly Val Cys Lys Gly Ile Phe Arg Thr
305                 310                 315                 320
Asp Gly Val Asp Glu Glu His Val Val Gln Leu Val Asp Thr Phe Pro
            325                 330                 335
Gly Gln Ser Ile Asp Phe Phe Gly Ala Leu Arg Ala Arg Val Tyr Asp
        340                 345                 350
Asp Glu Val Arg Arg Trp Val Ala Glu Thr Gly Val Glu Asn Ile Ala
    355                 360                 365
Lys Lys Leu Val Asn Ser Lys Asp Gly Pro Pro Thr Phe Glu Gln Pro
370                 375                 380
Lys Met Thr Ile Glu Lys Leu Leu Glu Tyr Gly His Met Leu Val Ala
385                 390                 395                 400
Glu Gln Glu Asn Val Lys Arg Val Gln Leu Ala Asp Lys Tyr Leu Asn
            405                 410                 415
Glu Ala Ala Leu Gly Ala Ala Asn Glu Asp Ala Met Lys Thr Gly Asn
        420                 425                 430
Phe Phe Lys
        435

<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggagtaaaga taatggcagt ggaggagaaa aaagagattg aag                    43

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtgatggtga tgatgtgatt gaaagaatgt gccacgttgg att                    43
```

```
<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggagtaaaga taatgctgga taacaaaatg gatggttttt acattgct                 48

<210> SEQ ID NO 6
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtgatggtga tgatgtttat ctgccagttg cacgcgttta aca                      43

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gggtatcaat ccaattcgga tgagtgctgg agaactcg                            38

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgagttctcc agcactcatc cgaattggat tgataccc                            38

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccgggaagca gccgatatca ttaagaaagg aaaaatg                             37

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10 cattttcct ttcttaatga tatcggctgc ttcccgg                              37
```

<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgtgaagatc gtattggtat ctgtacaggt attttccgca c                          41

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtgcggaaaa tacctgtaca gataccaata cgatcttcac g                          41

<210> SEQ ID NO 13
<211> LENGTH: 1149
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gcagccaaag aagtggacga acaaaagaa actgatggtg atcgttggaa aggccttgcg       60
tttgatatta gtgatgacca acaagatatt actcgtggta aaggcatgat tgattccttta    120 tttcaagcac ctatgggtga cggaacgcac gttgcagttt tatcttctta cgattatatt    180
tcccaaggtc aaaaaacata ttcaatggat aatactatgg acggttttta tattgcgcgc    240
ggttttatgg ataaactcgt ggttcatctc agcaaaaatt ttatgaaact tccaaacatt    300
aaagtaccgt taatcctggg catttgggga ggaaaaggtc aaggcaaatc atttcaatgt    360
gaattagtat ttgcgaaaat ggggattatt ccaattatga tgtctgcagg cgaattagaa    420
agcgggaatg cgggcgaacc agctaaaactt atccgtcagc gttatcgtga agcggctgat    480
ttaatctcaa aaggcaaaat gtcgtgtctc tttatcaatg atttagatgc gggcgctgga    540
cgtatgggcg ggacgactca atatactgtt aacaatcaaa tggtgaacgc taccctgatg    600
aatattgctg ataaccctac gaatgtacaa ttacctggca tgtataacaa agttgataac    660
gcacgcgtac cgattattgt cactggtaac gatttagca cccttacgc acccttatt       720 cgtgacggtc gcatggaaaa attttattgg gcaccaactc gggaggatcg catcggagtt    780
tgtaaaggca ttttcggac tgatggtgtt gatgaggaac atgttgtgca attagtggat    840
acgttccctg gtcaaagtat tgatttcttc ggcgccctcc gcgctcgtgt gtatgacgac    900
gaagtacgcc gctgggtcgc agaaactggt gttgaaaata tcgccaaaaa attagtaaat    960 tccaagacg gcccccctac tttcgaacaa cctaaaatga ctattgaaaa attattagaa    1020
tatggtcaca tgctggtagc agaacaagaa acgttaaac gcgtacaact tgccgataaa    1080
tacttgaatg aagcagcact tggagcagct aacgaagatg cgatgaaaac tggaaatttt    1140
tttaaataa                                                            1149

<210> SEQ ID NO 14

<211> LENGTH: 382
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Ala Ala Lys Glu Val Asp Glu Thr Lys Glu Thr Asp Gly Asp Arg Trp
1               5                   10                  15

Lys Gly Leu Ala Phe Asp Ile Ser Asp Gln Gln Asp Ile Thr Arg
            20                  25                  30

Gly Lys Gly Met Ile Asp Ser Leu Phe Gln Ala Pro Met Gly Asp Gly
        35                  40                  45

Thr His Val Ala Val Leu Ser Ser Tyr Asp Tyr Ile Ser Gln Gly Gln
    50                  55                  60

Lys Thr Tyr Ser Met Asp Asn Thr Met Asp Gly Phe Tyr Ile Ala Arg
65                  70                  75                  80

Gly Phe Met Asp Lys Leu Val Val His Leu Ser Lys Asn Phe Met Lys
                85                  90                  95

Leu Pro Asn Ile Lys Val Pro Leu Ile Leu Gly Ile Trp Gly Gly Lys
            100                 105                 110

Gly Gln Gly Lys Ser Phe Gln Cys Glu Leu Val Phe Ala Lys Met Gly
        115                 120                 125

Ile Ile Pro Ile Met Met Ser Ala Gly Glu Leu Glu Ser Gly Asn Ala
130                 135                 140

Gly Glu Pro Ala Lys Leu Ile Arg Gln Arg Tyr Arg Glu Ala Ala Asp
145                 150                 155                 160

Leu Ile Ser Lys Gly Lys Met Ser Cys Leu Phe Ile Asn Asp Leu Asp
                165                 170                 175

Ala Gly Ala Gly Arg Met Gly Gly Thr Thr Gln Tyr Thr Val Asn Asn
            180                 185                 190

Gln Met Val Asn Ala Thr Leu Met Asn Ile Ala Asp Asn Pro Thr Asn
        195                 200                 205

Val Gln Leu Pro Gly Met Tyr Asn Lys Val Asp Asn Ala Arg Val Pro
    210                 215                 220

Ile Ile Val Thr Gly Asn Asp Phe Ser Thr Leu Tyr Ala Pro Leu Ile
225                 230                 235                 240

Arg Asp Gly Arg Met Glu Lys Phe Tyr Trp Ala Pro Thr Arg Glu Asp
                245                 250                 255

Arg Ile Gly Val Cys Lys Gly Ile Phe Arg Thr Asp Gly Val Asp Glu
            260                 265                 270

Glu His Val Val Gln Leu Val Asp Thr Phe Pro Gly Gln Ser Ile Asp
        275                 280                 285

Phe Phe Gly Ala Leu Arg Ala Arg Val Tyr Asp Asp Glu Val Arg Arg
    290                 295                 300

Trp Val Ala Glu Thr Gly Val Glu Asn Ile Ala Lys Lys Leu Val Asn
305                 310                 315                 320

Ser Lys Asp Gly Pro Pro Thr Phe Glu Gln Pro Lys Met Thr Ile Glu
                325                 330                 335

Lys Leu Leu Glu Tyr Gly His Met Leu Val Ala Glu Gln Glu Asn Val
            340                 345                 350

Lys Arg Val Gln Leu Ala Asp Lys Tyr Leu Asn Glu Ala Ala Leu Gly
        355                 360                 365

Ala Ala Asn Glu Asp Ala Met Lys Thr Gly Asn Phe Phe Lys
```

```
<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggagtaaaga taatggcagc caaagaagtg gacgaaacaa aa                       42

<210> SEQ ID NO 16
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggagtaaaga taatgtcaat ggataatact atggacggct tttatattg                49

<210> SEQ ID NO 17
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtgatggtga tgatgtttaa aaaaatttcc agttttcatc gcatcttcgt ta            52

<210> SEQ ID NO 18
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtgatggtga tgatgtttat cggcaagttg tacgcgttta acg                      43

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggggattatt ccaattcgga tgtctgcagg cgaattag                            38

<210> SEQ ID NO 20
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
cgttatcgtg aagcggctga tatcatctca aaaggcaaaa tgtc                     44
```

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggaggatcgc atcggaattt gtaaaggcat ttttcgg                              37

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctaattcgcc tgcagacatc cgaattggaa taatcccc                             38

<210> SEQ ID NO 23
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gacattttgc cttttgagat gatatcagcc gcttcacgat aacg                      44

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ccgaaaaatg cctttacaaa ttccgatgcg atcctcc                              37

<210> SEQ ID NO 25
<211> LENGTH: 384
<212> TYPE: PRT
<213> ORGANISM: Nicotiana sp.

<400> SEQUENCE: 25

Ala Glu Gln Ile Asp Val Asp Pro Lys Lys Gln Thr Asp Ser Asp Arg
1               5                   10                  15

Trp Lys Gly Leu Val Gln Asp Phe Ser Asp Asp Gln Gln Asp Ile Thr
            20                  25                  30

Arg Gly Lys Gly Met Val Asp Ser Leu Phe Gln Ala Pro Thr Gly Thr
        35                  40                  45

Gly Thr His His Ala Val Leu Gln Ser Tyr Glu Tyr Val Ser Gln Gly
    50                  55                  60

Leu Arg Gln Tyr Asn Leu Asp Asn Lys Leu Asp Gly Phe Tyr Ile Ala
65                  70                  75                  80

Pro Ala Phe Met Asp Lys Leu Val Val His Ile Thr Lys Asn Phe Leu
                85                  90                  95

```
Lys Leu Pro Asn Ile Lys Val Pro Leu Ile Leu Gly Ile Trp Gly Gly
            100                 105                 110

Lys Gly Gln Gly Lys Ser Phe Gln Cys Glu Leu Val Phe Arg Lys Met
        115                 120                 125

Gly Ile Asn Pro Ile Met Met Ser Ala Gly Glu Leu Glu Ser Gly Asn
    130                 135                 140

Ala Gly Glu Pro Ala Lys Leu Ile Arg Gln Arg Tyr Arg Glu Ala Ala
145                 150                 155                 160

Glu Ile Ile Arg Lys Gly Asn Met Cys Cys Leu Phe Ile Asn Asp Leu
                165                 170                 175

Asp Ala Gly Ala Gly Arg Met Gly Gly Thr Thr Gln Tyr Thr Val Asn
        180                 185                 190

Asn Gln Met Val Asn Ala Thr Leu Met Asn Ile Ala Asp Asn Pro Thr
    195                 200                 205

Asn Val Gln Leu Pro Gly Met Tyr Asn Lys Gln Glu Asn Ala Arg Val
    210                 215                 220

Pro Ile Ile Val Thr Gly Asn Asp Phe Ser Thr Leu Tyr Ala Pro Leu
225                 230                 235                 240

Ile Arg Asp Gly Arg Met Glu Lys Phe Tyr Trp Ala Pro Thr Arg Glu
                245                 250                 255

Asp Arg Ile Gly Val Cys Thr Gly Ile Phe Arg Thr Asp Asn Val Pro
        260                 265                 270

Ala Glu Asp Val Val Lys Ile Val Asp Asn Phe Pro Gly Gln Ser Ile
    275                 280                 285

Asp Phe Phe Gly Ala Leu Arg Ala Arg Val Tyr Asp Asp Glu Val Arg
    290                 295                 300

Lys Trp Val Ser Gly Thr Gly Ile Glu Lys Ile Gly Asp Lys Leu Leu
305                 310                 315                 320

Asn Ser Phe Asp Gly Pro Pro Thr Phe Glu Gln Pro Lys Met Thr Ile
                325                 330                 335

Glu Lys Leu Leu Glu Tyr Gly Asn Met Leu Val Gln Glu Gln Glu Asn
        340                 345                 350

Val Lys Arg Val Gln Leu Ala Asp Lys Tyr Leu Lys Glu Ala Ala Leu
    355                 360                 365

Gly Asp Ala Asn Ala Asp Ala Ile Asn Asn Gly Ser Phe Phe Ala Ser
    370                 375                 380

<210> SEQ ID NO 26
<211> LENGTH: 383
<212> TYPE: PRT
<213> ORGANISM: Arabidopsis thaliana

<400> SEQUENCE: 26

Ala Val Lys Glu Asp Lys Gln Thr Asp Gly Asp Arg Trp Arg Gly Leu
1               5                   10                  15

Ala Tyr Asp Thr Ser Asp Gln Gln Asp Ile Thr Arg Gly Lys Gly
            20                  25                  30

Met Val Asp Ser Val Phe Gln Ala Pro Met Gly Thr Gly Thr His His
        35                  40                  45

Ala Val Leu Ser Ser Tyr Glu Tyr Val Ser Gln Gly Leu Arg Gln Tyr
    50                  55                  60

Asn Leu Asp Asn Met Met Asp Gly Phe Tyr Ile Ala Pro Ala Phe Met
65                  70                  75                  80

Asp Lys Leu Val Val His Ile Thr Lys Asn Phe Leu Thr Leu Pro Asn
                85                  90                  95
```

```
Ile Lys Val Pro Leu Ile Leu Gly Ile Trp Gly Gly Lys Gly Gln Gly
            100                 105                 110

Lys Ser Phe Gln Cys Glu Leu Val Met Ala Lys Met Gly Ile Asn Pro
            115                 120                 125

Ile Met Met Ser Ala Gly Glu Leu Ser Gly Asn Ala Gly Glu Pro
        130                 135                 140

Ala Lys Leu Ile Arg Gln Arg Tyr Arg Glu Ala Ala Asp Leu Ile Lys
145                 150                 155                 160

Lys Gly Lys Met Cys Cys Leu Phe Ile Asn Asp Leu Asp Ala Gly Ala
                165                 170                 175

Gly Arg Met Gly Gly Thr Thr Gln Tyr Thr Val Asn Asn Gln Met Val
            180                 185                 190

Asn Ala Thr Leu Met Asn Ile Ala Asp Asn Pro Thr Asn Val Gln Leu
            195                 200                 205

Pro Gly Met Tyr Asn Lys Glu Glu Asn Ala Arg Val Pro Ile Ile Cys
        210                 215                 220

Thr Gly Asn Asp Phe Ser Thr Leu Tyr Ala Pro Leu Ile Arg Asp Gly
225                 230                 235                 240

Arg Met Glu Lys Phe Tyr Trp Ala Pro Thr Arg Glu Asp Arg Ile Gly
                245                 250                 255

Val Cys Lys Gly Ile Phe Arg Thr Asp Lys Ile Lys Asp Glu Asp Ile
            260                 265                 270

Val Thr Leu Val Asp Gln Phe Pro Gly Gln Ser Ile Asp Phe Phe Gly
        275                 280                 285

Ala Leu Arg Ala Arg Val Tyr Asp Asp Glu Val Arg Lys Phe Val Glu
        290                 295                 300

Ser Leu Gly Val Glu Lys Ile Gly Lys Arg Leu Val Asn Ser Arg Glu
305                 310                 315                 320

Gly Pro Pro Val Phe Glu Gln Pro Glu Met Thr Tyr Glu Lys Leu Met
                325                 330                 335

Glu Tyr Gly Asn Met Leu Val Met Glu Gln Glu Asn Val Lys Arg Val
            340                 345                 350

Gln Leu Ala Glu Thr Tyr Leu Ser Gln Ala Ala Leu Gly Asp Ala Asn
            355                 360                 365

Ala Asp Ala Ile Gly Arg Gly Thr Phe Tyr Gly Lys Thr Glu Val
        370                 375                 380

<210> SEQ ID NO 27
<211> LENGTH: 385
<212> TYPE: PRT
<213> ORGANISM: Glycine max

<400> SEQUENCE: 27

Ala Val Glu Glu Lys Lys Glu Ile Glu Glu Thr Gln Gln Thr Asp Lys
1               5                   10                  15

Asp Arg Trp Lys Gly Leu Ala Tyr Asp Ile Ser Asp Gln Gln Asp
            20                  25                  30

Ile Thr Arg Gly Lys Gly Leu Val Asp Ser Leu Phe Gln Ala Pro Gln
            35                  40                  45

Asp Ala Gly Thr His Tyr Ala Val Met Ser Ser Tyr Glu Tyr Leu Ser
        50                  55                  60

Thr Gly Leu Arg Gln Tyr Leu Asp Asn Lys Met Asp Gly Phe Tyr Ile
65                  70                  75                  80

Ala Pro Ala Phe Met Asp Lys Leu Val Val His Ile Ser Lys Asn Phe
```

```
            85                  90                  95
Met Thr Leu Pro Asn Ile Lys Val Pro Leu Ile Leu Gly Ile Trp Gly
            100                 105                 110

Gly Lys Gly Gln Gly Lys Ser Phe Gln Cys Glu Leu Val Phe Ala Lys
        115                 120                 125

Met Gly Ile Asn Pro Ile Met Met Ser Ala Gly Leu Glu Ser Gly
    130                 135                 140

Asn Ala Gly Glu Pro Ala Lys Leu Ile Arg Gln Arg Tyr Arg Glu Ala
145                 150                 155                 160

Ala Asp Met Ile Lys Lys Gly Lys Met Cys Ala Leu Phe Ile Asn Asp
                165                 170                 175

Leu Asp Ala Gly Ala Gly Arg Leu Gly Gly Thr Thr Gln Tyr Thr Val
            180                 185                 190

Asn Asn Gln Met Val Asn Ala Thr Leu Met Asn Ile Ala Asp Asn Pro
        195                 200                 205

Thr Asn Val Gln Leu Pro Gly Met Tyr Asn Lys Glu Glu Asn Pro Arg
    210                 215                 220

Val Pro Ile Ile Val Thr Gly Asn Asp Phe Ser Thr Leu Tyr Ala Pro
225                 230                 235                 240

Leu Ile Arg Asp Gly Arg Met Glu Lys Phe Tyr Trp Ala Pro Thr Arg
                245                 250                 255

Glu Asp Arg Ile Gly Val Cys Thr Gly Ile Phe Arg Thr Asp Gly Ile
            260                 265                 270

Pro Glu Gln Asp Ile Val Lys Leu Val Asp Thr Phe Pro Gly Gln Ser
        275                 280                 285

Ile Asp Phe Phe Gly Ala Leu Arg Ala Arg Val Tyr Asp Asp Glu Val
    290                 295                 300

Arg Lys Trp Ile Ser Gly Val Gly Val Asp Ser Val Gly Lys Lys Leu
305                 310                 315                 320

Val Asn Ser Lys Asp Gly Pro Pro Thr Phe Glu Gln Pro Lys Met Thr
                325                 330                 335

Leu Glu Lys Leu Leu Leu Tyr Gly Asn Met Leu Val Gln Glu Gln Glu
            340                 345                 350

Asn Val Lys Arg Val Gln Leu Ala Asp Lys Tyr Leu Asn Glu Ala Ala
        355                 360                 365

Leu Gly Asn Ala Asn Glu Asp Ala Ile Gln Arg Gly Thr Phe Phe Gln
    370                 375                 380

Ser
385

<210> SEQ ID NO 28
<211> LENGTH: 420
<212> TYPE: PRT
<213> ORGANISM: Glycine max

<400> SEQUENCE: 28

Ala Ala Glu Lys Glu Ile Asp Glu Lys Gln Gln Thr Asp Lys Asp Arg
1               5                   10                  15

Trp Lys Gly Leu Ala Tyr Asp Val Ser Asp Asp Gln Gln Asp Ile Thr
            20                  25                  30

Arg Gly Lys Gly Leu Val Asp Ser Leu Phe Gln Ala Pro Gln Asp Thr
        35                  40                  45

Gly Thr His Tyr Ala Ile Met Ser Ser Tyr Glu Tyr Leu Ser Thr Gly
    50                  55                  60
```

Leu Lys Gln Tyr Asn Leu Asp Asn Asn Met Asp Gly Phe Tyr Ile Ala
65                  70                  75                  80

Pro Ala Phe Met Asp Lys Leu Val Val His Ile Ser Lys Asn Phe Met
            85                  90                  95

Thr Leu Pro Asn Ile Lys Val Pro Leu Ile Leu Gly Ile Trp Gly Gly
        100                 105                 110

Lys Gly Gln Gly Lys Ser Phe Gln Cys Glu Leu Val Phe Ala Lys Met
            115                 120                 125

Gly Ile Asn Pro Ile Met Met Ser Ala Gly Glu Leu Glu Ser Gly Asn
130                 135                 140

Ala Gly Glu Pro Ala Lys Leu Ile Arg Gln Arg Tyr Arg Glu Ala Ala
145                 150                 155                 160

Asp Met Ile Lys Lys Gly Lys Met Cys Ala Leu Phe Ile Asn Asp Leu
            165                 170                 175

Asp Ala Gly Ala Gly Arg Leu Gly Gly Thr Thr Gln Tyr Thr Val Asn
        180                 185                 190

Asn Gln Met Val Asn Ala Thr Leu Met Asn Ile Ala Asp Asn Pro Thr
            195                 200                 205

Asn Val Gln Leu Pro Gly Met Tyr Asn Lys Glu Glu Asn Pro Arg Val
210                 215                 220

Pro Ile Ile Val Thr Gly Asn Asp Phe Ser Thr Leu Tyr Ala Pro Leu
225                 230                 235                 240

Ile Arg Asp Gly Arg Met Glu Lys Phe Tyr Trp Ala Pro Thr Arg Asp
            245                 250                 255

Asp Arg Val Gly Val Cys Asn Gly Ile Phe Arg Thr Asp Asn Val Pro
        260                 265                 270

Lys Asp Asp Ile Val Lys Leu Val Asp Thr Phe Pro Gly Gln Ser Ile
            275                 280                 285

Asp Phe Phe Gly Ala Leu Arg Ala Arg Val Tyr Asp Asp Glu Val Arg
        290                 295                 300

Lys Trp Ile Ser Val Val Gly Val Asp Phe Ile Gly Lys Lys Leu Val
305                 310                 315                 320

Asn Ser Lys Glu Gly Pro Pro Thr Phe Asp Gln Pro Lys Met Thr Leu
            325                 330                 335

Ser Lys Leu Leu Glu Tyr Gly Asn Met Leu Val Gln Glu Gln Glu Asn
        340                 345                 350

Val Lys Arg Val Gln Leu Ala Asp Lys Tyr Leu Lys Glu Ala Ala Leu
            355                 360                 365

Gly Asp Ala Asn Gln Asp Ser Ile Asn Arg Gly Thr Phe Tyr Gly Lys
370                 375                 380

Ala Ala Gln Gln Val Asn Ile Pro Val Pro Glu Gly Cys Thr Asp Pro
385                 390                 395                 400

Asn Ala Ser Asn Phe Asp Pro Thr Ala Arg Ser Asp Asp Gly Thr Cys
            405                 410                 415

Leu Tyr Thr Pro
            420

<210> SEQ ID NO 29
<211> LENGTH: 382
<212> TYPE: PRT
<213> ORGANISM: Miscanthus giganteus

<400> SEQUENCE: 29

Ala Ala Lys Glu Val Asp Glu Thr Lys Glu Thr Asp Gly Asp Arg Trp
1               5                   10                  15

```
Lys Gly Leu Ala Phe Asp Ile Ser Asp Asp Gln Gln Asp Ile Thr Arg
            20                  25                  30

Gly Lys Gly Met Ile Asp Ser Leu Phe Gln Ala Pro Met Gly Asp Gly
        35                  40                  45

Thr His Val Ala Val Leu Ser Ser Tyr Asp Tyr Ile Ser Gln Gly Gln
    50                  55                  60

Lys Thr Tyr Ser Met Asp Asn Thr Met Asp Gly Phe Tyr Ile Ala Arg
65                  70                  75                  80

Gly Phe Met Asp Lys Leu Val Val His Leu Ser Lys Asn Phe Met Lys
                85                  90                  95

Leu Pro Asn Ile Lys Val Pro Leu Ile Leu Gly Ile Trp Gly Gly Lys
            100                 105                 110

Gly Gln Gly Lys Ser Phe Gln Cys Glu Leu Val Phe Ala Lys Met Gly
        115                 120                 125

Ile Ile Pro Ile Met Met Ser Ala Gly Glu Leu Glu Ser Gly Asn Ala
130                 135                 140

Gly Glu Pro Ala Lys Leu Ile Arg Gln Arg Tyr Arg Glu Ala Ala Asp
145                 150                 155                 160

Leu Ile Ser Lys Gly Lys Met Ser Cys Leu Phe Ile Asn Asp Leu Asp
                165                 170                 175

Ala Gly Ala Gly Arg Met Gly Gly Thr Thr Gln Tyr Thr Val Asn Asn
            180                 185                 190

Gln Met Val Asn Ala Thr Leu Met Asn Ile Ala Asp Asn Pro Thr Asn
        195                 200                 205

Val Gln Leu Pro Gly Met Tyr Asn Lys Val Asp Asn Ala Arg Val Pro
210                 215                 220

Ile Ile Val Thr Gly Asn Asp Phe Ser Thr Leu Tyr Ala Pro Leu Ile
225                 230                 235                 240

Arg Asp Gly Arg Met Glu Lys Phe Tyr Trp Ala Pro Thr Arg Glu Asp
                245                 250                 255

Arg Ile Gly Val Cys Lys Gly Ile Phe Arg Thr Asp Gly Val Asp Glu
            260                 265                 270

Glu His Val Val Gln Leu Val Asp Thr Phe Pro Gly Gln Ser Ile Asp
        275                 280                 285

Phe Phe Gly Ala Leu Arg Ala Arg Val Tyr Asp Asp Glu Val Arg Arg
290                 295                 300

Trp Val Ala Glu Thr Gly Val Glu Asn Ile Ala Lys Lys Leu Val Asn
305                 310                 315                 320

Ser Lys Asp Gly Pro Pro Thr Phe Glu Gln Pro Lys Met Thr Ile Glu
                325                 330                 335

Lys Leu Leu Glu Tyr Gly His Met Leu Val Ala Glu Gln Glu Asn Val
            340                 345                 350

Lys Arg Val Gln Leu Ala Asp Lys Tyr Leu Asn Glu Ala Ala Leu Gly
        355                 360                 365

Ala Ala Asn Glu Asp Ala Met Lys Thr Gly Asn Phe Phe Lys
    370                 375                 380

<210> SEQ ID NO 30
<211> LENGTH: 421
<212> TYPE: PRT
<213> ORGANISM: Miscanthus giganteus

<400> SEQUENCE: 30

Ala Met Ala Val Asn Lys Glu Val Asp Glu Thr Lys Gln Thr Glu Gln
```

-continued

```
1               5                    10                   15
Asp Arg Trp Arg Gly Leu Ala Tyr Asp Thr Ser Asp Gln Gln Asp
                20                  25                  30
Ile Thr Arg Gly Lys Gly Arg Val Asp Pro Leu Phe Gln Ala Pro Met
                35                  40                  45
Gly Asp Gly Thr His Val Ala Val Leu Ser Ser Tyr Asp Tyr Ile Ser
                50                  55                  60
Gln Gly Leu Arg Gln Tyr Ser Phe Asp Asn Thr Met Asp Gly Tyr Tyr
65                              70                  75                  80
Ile Ala Pro Ala Phe Met Asp Lys Leu Val Val His Ile Ala Lys Asn
                    85                  90                  95
Phe Met Thr Leu Pro Asn Ile Lys Val Pro Leu Ile Leu Gly Ile Trp
                100                 105                 110
Gly Gly Lys Gly Gln Gly Lys Ser Phe Gln Cys Glu Leu Val Phe Ala
                115                 120                 125
Lys Met Gly Ile Asn Pro Ile Val Met Ser Ala Gly Glu Leu Glu Ser
                130                 135                 140
Gly Asn Ala Gly Glu Pro Ala Lys Leu Ile Arg Gln Arg Tyr Arg Glu
145                 150                 155                 160
Ala Ala Asp Met Ile Lys Lys Gly Lys Met Cys Val Leu Phe Ile Asn
                    165                 170                 175
Asp Leu Asp Ala Gly Ala Gly Arg Met Gly Gly Thr Thr Gln Tyr Thr
                180                 185                 190
Val Asn Asn Gln Met Val Asn Ala Thr Leu Met Asn Ile Ala Asp Asn
                195                 200                 205
Pro Thr Asn Val Gln Leu Pro Gly Met Tyr Asn Lys Val Asp Asn Ala
210                 215                 220
Arg Val Pro Ile Ile Val Thr Gly Asn Asp Phe Ser Thr Leu Tyr Ala
225                 230                 235                 240
Pro Leu Ile Arg Asp Gly Arg Met Glu Lys Glu Tyr Trp Ala Pro Thr
                    245                 250                 255
Arg Glu Asp Arg Val Gly Val Cys Lys Gly Ile Phe Arg Thr Asp Gly
                    260                 265                 270
Val Pro Asp Glu His Val Val Gln Leu Val Asp Ala Phe Pro Gly Gln
                275                 280                 285
Ser Ile Asp Glu Phe Gly Ala Leu Arg Ala Arg Val Tyr Asp Asp Glu
                290                 295                 300
Val Arg Arg Trp Val Ala Glu Thr Gly Val Glu Asn Ile Ala Arg Arg
305                 310                 315                 320
Leu Val Asn Ser Lys Glu Gly Pro Pro Thr Phe Glu Gln Pro Arg Met
                    325                 330                 335
Thr Leu Asp Lys Leu Met Glu Tyr Gly Arg Met Leu Val Glu Glu Gln
                    340                 345                 350
Glu Asn Val Lys Arg Val Gln Leu Ala Asp Lys Tyr Leu Thr Glu Ala
                355                 360                 365
Ala Leu Gly Asp Ala Asn Asp Ala Ile Ile Arg Gly Asp Leu Tyr
                370                 375                 380
Gly Lys Ala Ala Gln Gln Val Arg Val Pro Val Pro Glu Gly Cys Thr
385                 390                 395                 400
Asp Pro Lys Ala Gly Asn Phe Asp Pro Ala Ala Arg Ser Asp Asp Gly
                    405                 410                 415
Ser Cys Val Tyr Asn
                420
```

<210> SEQ ID NO 31
<211> LENGTH: 292
<212> TYPE: PRT
<213> ORGANISM: Glycine max

<400> SEQUENCE: 31

Leu Asp Asn Lys Met Asp Gly Phe Tyr Ile Ala Pro Ala Phe Met Asp
1               5                   10                  15

Lys Leu Val Val His Ile Ser Lys Asn Phe Met Thr Leu Pro Asn Ile
            20                  25                  30

Lys Val Pro Leu Ile Leu Gly Ile Trp Gly Gly Lys Gly Gln Gly Lys
        35                  40                  45

Ser Phe Gln Cys Glu Leu Val Phe Ala Lys Met Gly Ile Asn Pro Ile
    50                  55                  60

Met Met Ser Ala Gly Glu Leu Glu Ser Gly Asn Ala Gly Glu Pro Ala
65                  70                  75                  80

Lys Leu Ile Arg Gln Arg Tyr Arg Glu Ala Ala Asp Met Ile Lys Lys
                85                  90                  95

Gly Lys Met Cys Ala Leu Phe Ile Asn Asp Leu Asp Ala Gly Ala Gly
            100                 105                 110

Arg Leu Gly Gly Thr Thr Gln Tyr Thr Val Asn Asn Gln Met Val Asn
        115                 120                 125

Ala Thr Leu Met Asn Ile Ala Asp Asn Pro Thr Asn Val Gln Leu Pro
    130                 135                 140

Gly Met Tyr Asn Lys Glu Glu Asn Pro Arg Val Pro Ile Ile Val Thr
145                 150                 155                 160

Gly Asn Asp Phe Ser Thr Leu Tyr Ala Pro Leu Ile Arg Asp Gly Arg
                165                 170                 175

Met Glu Lys Phe Tyr Trp Ala Pro Thr Arg Glu Asp Arg Ile Gly Val
            180                 185                 190

Cys Thr Gly Ile Phe Arg Thr Asp Gly Ile Pro Glu Gln Asp Ile Val
        195                 200                 205

Lys Leu Val Asp Thr Phe Pro Gly Gln Ser Ile Asp Phe Phe Gly Ala
    210                 215                 220

Leu Arg Ala Arg Val Tyr Asp Asp Glu Val Arg Lys Trp Ile Ser Gly
225                 230                 235                 240

Val Gly Val Asp Ser Val Gly Lys Lys Leu Val Asn Ser Lys Asp Gly
                245                 250                 255

Pro Pro Thr Phe Glu Gln Pro Lys Met Thr Leu Glu Lys Leu Leu Leu
            260                 265                 270

Tyr Gly Asn Met Leu Val Gln Glu Gln Glu Asn Val Lys Arg Val Gln
        275                 280                 285

Leu Ala Asp Lys
    290

<210> SEQ ID NO 32
<211> LENGTH: 1155
<212> TYPE: DNA
<213> ORGANISM: Glycine max
<220> FEATURE:
<221> NAME/KEY: CDS
<222> LOCATION: (1)..(1155)

<400> SEQUENCE: 32 gca gtg gag gag aaa aaa gag att gaa gaa act caa caa acc gac aaa     48
Ala Val Glu Glu Lys Lys Glu Ile Glu Glu Thr Gln Gln Thr Asp Lys -continued

```
1               5                   10                  15
gat cgc tgg aaa ggc tta gcc tat gat att agc gat gat cag cag gat       96
Asp Arg Trp Lys Gly Leu Ala Tyr Asp Ile Ser Asp Asp Gln Gln Asp
             20                  25                  30 atc acc cgc ggg aaa ggc ctt gtg gac agt ctg ttt caa gca cct caa      144
Ile Thr Arg Gly Lys Gly Leu Val Asp Ser Leu Phe Gln Ala Pro Gln
         35                  40                  45 gat gca ggt acg cac tac gcc gtc atg tca agt tat gaa tac tta agc      192
Asp Ala Gly Thr His Tyr Ala Val Met Ser Ser Tyr Glu Tyr Leu Ser
     50                  55                  60 acc ggt ctt cgt cag tat ctg gat aac aaa atg gat ggt ttt tac att      240
Thr Gly Leu Arg Gln Tyr Leu Asp Asn Lys Met Asp Gly Phe Tyr Ile
 65                  70                  75                  80 gct ccg gcg ttt atg gac aaa tta gtg gta cac atc tcg aag aac ttc      288
Ala Pro Ala Phe Met Asp Lys Leu Val Val His Ile Ser Lys Asn Phe
                 85                  90                  95 atg acg ctg cca aat atc aaa gtt cca ctg att tta gga att tgg ggc      336
Met Thr Leu Pro Asn Ile Lys Val Pro Leu Ile Leu Gly Ile Trp Gly
            100                 105                 110 ggt aag ggg caa ggg aaa agt ttt cag tgt gaa ctg gtg ttt gcg aaa      384
Gly Lys Gly Gln Gly Lys Ser Phe Gln Cys Glu Leu Val Phe Ala Lys
        115                 120                 125 atg ggt atc aat cca att atg atg agt gct gga gaa ctc gaa agc ggt      432
Met Gly Ile Asn Pro Ile Met Met Ser Ala Gly Glu Leu Glu Ser Gly
    130                 135                 140 aac gcg ggt gaa cct gcc aaa ctg atc cgt cag cgc tac cgg gaa gca      480
Asn Ala Gly Glu Pro Ala Lys Leu Ile Arg Gln Arg Tyr Arg Glu Ala
145                 150                 155                 160 gcc gat atg att aag aaa gga aaa atg tgc gcc ctg ttt atc aac gat      528
Ala Asp Met Ile Lys Lys Gly Lys Met Cys Ala Leu Phe Ile Asn Asp
                165                 170                 175 ttg gat gct ggc gct ggt cgt ctc ggt ggt acc acg caa tat act gtg      576
Leu Asp Ala Gly Ala Gly Arg Leu Gly Gly Thr Thr Gln Tyr Thr Val
            180                 185                 190 aac aac caa atg gtg aac gcg acc ctg atg aac att gca gat aac ccg      624
Asn Asn Gln Met Val Asn Ala Thr Leu Met Asn Ile Ala Asp Asn Pro
        195                 200                 205 acc aac gtt caa ctg cct ggc atg tat aac aag gaa gaa aac ccc cgc      672
Thr Asn Val Gln Leu Pro Gly Met Tyr Asn Lys Glu Glu Asn Pro Arg
    210                 215                 220 gta ccg att att gta acg ggc aat gat ttc tcg act ctg tat gcc ccg      720
Val Pro Ile Ile Val Thr Gly Asn Asp Phe Ser Thr Leu Tyr Ala Pro
225                 230                 235                 240 ctc att cgt gat gga cgt atg gag aaa ttc tac tgg gct cca aca cgt      768
Leu Ile Arg Asp Gly Arg Met Glu Lys Phe Tyr Trp Ala Pro Thr Arg
                245                 250                 255 gaa gat cgt att ggt gtg tgt aca ggt att ttc cgc aca gat ggc atc      816
Glu Asp Arg Ile Gly Val Cys Thr Gly Ile Phe Arg Thr Asp Gly Ile
            260                 265                 270 ccg gaa caa gac atc gtt aaa ctt gtg gat act ttt cct ggt cag agc      864
Pro Glu Gln Asp Ile Val Lys Leu Val Asp Thr Phe Pro Gly Gln Ser
        275                 280                 285 atc gac ttt ttt ggg gca ttg cgc gcc cgt gta tat gat gat gaa gtg      912
Ile Asp Phe Phe Gly Ala Leu Arg Ala Arg Val Tyr Asp Asp Glu Val
    290                 295                 300 cgt aaa tgg att agc ggc gta ggc gtc gat agt gtg ggt aaa aaa ctt      960
Arg Lys Trp Ile Ser Gly Val Gly Val Asp Ser Val Gly Lys Lys Leu
305                 310                 315                 320 gtt aat tcc aaa gat ggc ccc ccg acc ttc gaa caa cca aaa atg acc     1008
```

```
                                                                                    1056
ctt gaa aaa ctg ctg ctg tat ggt aat atg tta gtc caa gag caa gaa
Leu Glu Lys Leu Leu Leu Tyr Gly Asn Met Leu Val Gln Glu Gln Glu
            340                 345                 350

1104
aat gtt aaa cgc gtg caa ctg gca gat aaa tac ctc aat gaa gcg gcc
Asn Val Lys Arg Val Gln Leu Ala Asp Lys Tyr Leu Asn Glu Ala Ala
            355                 360                 365

1152
tta ggt aat gcg aac gag gac gca atc caa cgt ggc aca ttc ttt caa
Leu Gly Asn Ala Asn Glu Asp Ala Ile Gln Arg Gly Thr Phe Phe Gln
        370                 375                 380 tca                                                                                 1155
Ser
385
```

Val Asn Ser Lys Asp Gly Pro Pro Thr Phe Glu Gln Pro Lys Met Thr
            325             330             335

```
<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 33

His His His His His His
1               5
```

What is claimed is:

1. A modified rubisco activase comprising a point mutation at amino acid positions 135 or 163 based on the sequence according to SEQ ID NO: 31, wherein the modified rubisco activase has a melting temperature greater than about 30.4° C.

2. The modified rubisco activase of claim 1, wherein the point mutation at amino acid position 135 results in a substitution of R for the naturally occurring amino acid at this position, wherein the point mutation at amino acid position 163 results in a substitution of I for the naturally occurring amino acid at this position.

3. The modified rubisco activase of claim 1, wherein the modified rubisco activase further comprises a point mutation at amino acid position 262 based on the sequence according to SEQ ID NO: 31.

4. The modified rubisco activase of claim 1, wherein the modified rubisco activase is soy β rubisco activase.

5. The modified rubisco activase of claim 2, wherein the modified rubisco activase comprises the point mutations at amino acid positions 135, 163, and further comprises a point mutation at amino acid position 262 according to SEQ ID NO: 31, wherein the point mutation at amino acid position 262 results in a substitution of I for the naturally occurring amino acid at this position.

6. The modified rubisco activase of claim 2, wherein the modified rubisco activase comprises point mutations at positions 135 and 163 based on the sequence according to SEQ ID NO: 31.

7. The modified rubisco activase of claim 1, wherein the modified rubisco activase is Miscanthus β rubisco activase according to SEQ ID NO: 2, and wherein the amino acid positions 135 and 162 based on SEQ ID NO: 31 respectively correspond to amino acid positions 133 and 161 in SEQ ID NO: 2.

8. The modified rubisco activase of claim 7, wherein the modified rubisco activase has a melting temperature greater than about 39.8° C.

9. The modified rubisco activase of claim 7, wherein the point mutation at amino acid position 133 results in a substitution of R for the naturally occurring amino acid at this position, wherein the point mutation at amino acid position 161 results in a substitution of I for the naturally occurring amino acid at this position.

10. The modified rubisco activase of claim 7, wherein the modified rubisco activase comprises point mutations at amino acid positions 133 and 161, and further comprises a point mutation at position 260 in SEQ ID NO: 2 that corresponds to position 262 according to SEQ ID NO: 31.

11. The modified rubisco activase of claim 1, wherein the modified rubisco activase has a melting temperature greater than about 34.5° C.

12. The modified rubisco activase of claim 1, wherein the modified rubisco activase has a melting temperature greater than about 34.9° C.

13. The modified rubisco activase of claim 1, wherein the modified rubisco activase has a melting temperature greater than about 38.8° C.

14. The modified rubisco activase of claim 1, wherein the modified rubisco activase has a melting temperature greater than about 42.8° C.

15. The modified rubisco activase of claim 1, wherein the modified rubisco activase has a melting temperature greater than about 44.0° C.

16. The modified rubisco activase of claim 1, wherein the modified rubisco activase has a melting temperature greater than about 44.4° C.

17. The modified rubisco activase of claim 1, wherein the modified rubisco activase has a melting temperature greater than about 46.0° C.

18. An isolated polynucleotide encoding the modified rubisco activase of claim 1.

19. A recombinant expression system comprising the isolated polynucleotide of claim 18.

20. A plant cell transfected with the recombinant expression system of claim 19.

21. A genetically modified plant expressing the isolated polynucleotide of claim 18.

22. The genetically modified plant of claim 21, wherein the genetically modified plant is a genetically modified *Arabidospis*.

23. The genetically modified plant of claim 21, wherein the genetically modified plant is a genetically modified soybean plant.

24. The genetically modified plant of claim 21, wherein the genetically modified plant is a genetically modified *Miscanthus giganteus*.

* * * * *

UNITED STATES PATENT AND TRADEMARK OFFICE
CERTIFICATE OF CORRECTION

PATENT NO. : 10,487,368 B2
APPLICATION NO. : 15/690247
DATED : November 26, 2019
INVENTOR(S) : Phani R. Pokkuluri et al.

It is certified that error appears in the above-identified patent and that said Letters Patent is hereby corrected as shown below:

On the Title Page

Item (72):
Replace "Andrej JOACHIMIAK, Bollingbrook, IL (US)"
With --Andrzej JOACHIMIAK, Bollingbrook, IL (US)--

Signed and Sealed this
Seventh Day of February, 2023

Katherine Kelly Vidal
*Director of the United States Patent and Trademark Office*